United States Patent
Laborie et al.

(10) Patent No.: US 7,968,646 B2
(45) Date of Patent: Jun. 28, 2011

(54) METHOD OF IN SITU BIOPRODUCTION AND COMPOSITION OF BACTERIAL CELLULOSE NANOCOMPOSITES

(75) Inventors: Marie-Pierre Laborie, Pullman, WA (US); Elvie Brown, Pasco, WA (US)

(73) Assignee: Washington State University, Pullman, WA (US)

( * ) Notice: Subject to any disclaimer, the term of this patent is extended or adjusted under 35 U.S.C. 154(b) by 75 days.

(21) Appl. No.: 12/197,098

(22) Filed: Aug. 22, 2008

(65) Prior Publication Data

US 2009/0192264 A1    Jul. 30, 2009

Related U.S. Application Data

(60) Provisional application No. 60/957,279, filed on Aug. 22, 2007.

(51) Int. Cl.
*C08B 37/06* (2006.01)
(52) U.S. Cl. .................................. 525/54.21
(58) Field of Classification Search ............... 525/54.21
See application file for complete search history.

(56) References Cited

U.S. PATENT DOCUMENTS

| | | | |
|---|---|---|---|
| 4,584,357 A | 4/1986 | Harding | |
| 4,912,049 A | 3/1990 | Farah | |
| 5,245,024 A | 9/1993 | Scarpa | |
| 6,069,136 A | 5/2000 | Tahara | |
| 2005/0037082 A1* | 2/2005 | Wan et al. | 424/488 |
| 2006/0094320 A1* | 5/2006 | Chen et al. | 442/340 |

FOREIGN PATENT DOCUMENTS

| WO | WO 86/02095 | 4/1986 |
|---|---|---|
| WO | WO 89/08148 | 9/1989 |

OTHER PUBLICATIONS

Astley et al., "Tensile deformation of bacterial cellulose composites," International Journal of Biological Macromolecules, 2003, pp. 28-35, vol. 32.
Atalla et al., "Native Cellulose: A Composite of Two Distinct Crystalline Forms," Science, 1984, pp. 283-285, vol. 223.
Bochek et al., "Cellulose Solubility Parameters," Cellulose Chemistry and Technology, 1993, pp. 583-596, vol. 27.
Brown, "The Biosynthesis of Cellulose," Journal of Macromolecular Science, Pure and Applied Chemistry., 1996, pp. 1345-1373, vol. A33.
Canale-Parola et al., "Studies on *Sarcina ventriculi*. I. Stock Culture Method," Journal of Bacteriology, 1960, pp. 857-859, vol. 79.
Cannon et al., "Biogenesis of Bacterial Cellulose," Microbiology, 1991, pp. 435-447, vol. 17.
Choi et al., "Preparation and characterization of acrylic acid-treated bacterial cellulose cation-exchange membrane," Journal of Chemical Technology and Biotechnology, 2004, pp. 79-84, vol. 79.
Coleman et al., "Mechanical Reinforcement of Polymers Using Carbon Nanotubes," Advanced Materials, 2006, pp. 689-706, vol. 18.
Colvin et al., "Congo Red and Calcoflur White Inhibition of *Acetobacter xylinum* Cell Growth and of Bacterial Cellulose Microfibril Formation: Isolation and Properties of a Transient, Extracellular Glucan Related to Cellulose," Protoplasm, 1983, pp. 34-40, vol. 116.
Czaja et al., "The Future Prospects of Microbial Cellulose in Biomedical Applications," Biomacromolecules, 2007, pp. 1-12, vol. 8.
De Baets et al., "Cellulose production by *Acetobacter xylinum*: Fermentation Optimisation and Application Potential," Mededelingen, 1997 pp. 1231-1238, vol. 62.
Favier et al., "Polymer Nanocomposites Reinforced by Cellulose Whiskers," Macromolecules, 1995, pp. 6365-6367, vol. 28.
Fedors, "A Method for Estimating Both the Solubility Parameters and Molar Volumes of Liquids. Supplment," Polymer Engineering and Science, 1974, p. 472, vol. 14.
George et al., "Characterization of chemically treated bacterial (*Acetobacter xylinum*) biopolymer: Some thermo-mechanical properties," Biological Macromolecules, 2005, pp. 189-194, vol. 37.
Haigler et al., Alteration of In Vivo Cellulose Ribbon Assembly by Carboxymethylcellulose and other Cellulose Derivatives, The Journal of Cell Biology, 1982, pp. 64-69, vol. 94.
Haigler et al., "Calcoflur White ST Alters the in vivo Assembly of Cellulose Microfibrils," Science, 1980, pp. 903-906, vol. 210.
Hestrin et al., "Synthesis of Cellulose by *Acetobacter xylinum*. 2. Preparation of Freeze-Dried Cells Capable of Polymerizing Glucose to Cellulose," Biochemical Journal, 1954, pp. 345-352, vol. 58.

(Continued)

*Primary Examiner* — Ling-Siu Choi
*Assistant Examiner* — Sonya Wright
(74) *Attorney, Agent, or Firm* — Barry L. Davison; Davis Wright Tremaine LLP

(57) ABSTRACT

Provided are novel methods for making cellulose nanocomposites, comprising biosynthesis of cellulose fibrils in situ using a growth medium comprising a polymer matrix material, under conditions suitable to provide for dispersion of the fibril throughout the growth medium as the fibrils are being formed to provide a cellulose nanocomposite material or film wherein the cellulose fibrils are highly or uniformly dispersed in the cellulose nanocomposite material, and wherein fibril structure and/or nanocomposite composition is customizable. Certain method aspects further comprise removing or separating the cellulose nanocomposite material or film from the medium, and may further comprise washing the cellulose nanocomposite material or film to remove residual medium. Particular aspects further comprise freeze-drying the cellulose nanocomposite material or film, and/or further comprise forming a molded product using the cellulose nanocomposite material or film. Compositions made by the methods are provided.

16 Claims, 19 Drawing Sheets

OTHER PUBLICATIONS

Hoffman et al., "Melting Process and the Equilibrium Melting Temperature of Polychlorotrifluoroethylene," Journal of Research of the National Bureau of Standards—A. Physics and Chemistry, 1962, pp. 13-28, vol. 66A.

Hoy, "New Values of the Solubility Parameters From Vapor Pressure Data," Journal of Paint Technology, 1970, pp. 76-118, vol. 42.

Jonas et al., "Production and application of microbial cellulose," Polymer Degradation and Stability, 1998, pp. 101-106, vol. 59.

Joseph et al., "Effects of polyacrylamide-co-acrylic acid on cellulose production by *Acetobacter xylinum*," Journal of Chemical Technology and Biotechnology, 2003, pp. 964-970, vol. 78.

Kataoka et al., "Quantitative analysis for the cellulose Iα crystalline phase in developing wood cell walls," International Journal of Biological Macromolecules, 1999, pp. 37-41, vol. 24.

Klemm et al., "Bacterial synthesized cellulose—artificial blood vessels for microsurgery," Progress in Polymer Science, 2001, pp. 1561-1603, vol. 26.

Matthysse et al., "Genes Required for Cellulose Synthesis in *Agrobacterium tumefaciens*," Journal of Bacteriology, 1995, pp. 1069-1075, vol. 177.

Napoli et al., "Production of Cellulose Microfibrils by *Rhizobium*," Applied Microbiology, 1975, pp. 123-131, vol. 30.

Ohad, "Biosynthesis of Cellulose. VII. The Interaction of Soluble Carboxymethylcellulose with Cellulose Fibres," Bulletin of Research Council of Israel, 1963, pp. 279-285, vol. 11A4.

Orts et al., "Application of Cellulose Microfibrils in Polymer Nanocomposites," Journal of Polymers and the Environment, 2005, pp. 301-306, vol. 13.

Podsiadlo et al., "Molecularly Engineered Nanocomposites: Layer-by-Layer Assembly of Cellulose Nanocrystals," Biomacromolecules, 2005, pp. 2914-2918, vol. 6.

Samir et al., "Nanocomposite Polymer Electrolytes based on Poly(oxyethylene) and Cellulose Whiskers," Polimeros: Ciencia e Tecnologia, 2005, pp. 109-113, vol. 15.

Samir et al., "Review of Recent Research into Cellulosic Whiskers, Their Properties and Their Application in Nanocomposite Field," Biomacromolecules, 2005, pp. 612-626, vol. 6.

Shoda et al., "Recent Advances in Bacterial Cellulose Production," Biotechnology and Bioprocess Engineering, 2005, pp. 1-8, vol. 10.

Silva et al., "Flory-Huggins interaction parameter of poly(ethylene oxide)/poly(epichlorohydrin) and poly(ethylene oxide)/poly(epichlorohydrin-co-ethylene oxide) blends," Polymer, 1998, pp. 2551-2556, vol. 39.

Small, "Some Factors Affecting the Solubility of Polymers," Journal of Applied Chemistry, 1953, pp. 71-80, vol. 3.

Smart et al., "The biocompatibility of carbon nanotubes," Carbon, 2006, pp. 1034-1047, vol. 44.

Spiers et al., "Biofilm formation at the air-liquid interface by the *Pseudomonas fluorescens* SBW25 wrinkly spreader requires an acetylated form of cellulose," Molecular Microbiology, 2003, pp. 15-27, vol. 50.

Sugiyama et al., "Transformation of Valonia Cellulose Crystals by an Alkaline Hydrothermal Treatment," Macromolecules, 1990, pp. 3196-3198, vol. 23.

Tonouchi et al., "Addition of a Small Amount of an Endoglucanase Enhances Cellulose Production by *Acetobacter xylinum*," Bioscience, Biotechnology and Biochemistry, 1995, pp. 805-808, vol. 59.

Udhardt et al., "Analytical Investigations of Bacterial Cellulose," Macromolecular Symposia, 2005, pp. 201-212, vol. 223.

Uhlin et al., "Influence of hemicelluloses on the aggregation patterns of bacterial cellulose," Cellulose, 1995, pp. 129-144, vol. 2.

Webb et al., "The Effect of Bacterial Cell Lysis and of Plant Extracts on Cellulose Production by *Acetobacter xylinum*," Canadian Journal of Biochemistry and Physiology, 1963, pp. 1691-1702, vol. 41.

Whitney et al., "Roles of Cellulose and Xyloglucan in Determining the Mechanical Properties of Primary Plan Cell Walls," Plant Physiology, 1999, pp. 657-663, vol. 121.

Whitney et al., "Structural aspects of the interaction of mannan-based polysaccharides with bacterial cellulose," Carbohydrate Research, 1998, pp. 299-309, vol. 307.

Yamamoto et al., "In Situ crystallization of bacterial cellulose I. Influences of polymeric additives, stirring and temperature on the formation celluloses $I_\alpha$ and $I_\beta$ as revealed by cross polarization/magic angle spinning (CP/MAS) $^{13}$C NMR spectroscopy," Cellulose, 1994, pp. 57-66, vol. 1.

Yamamoto et al., "In Situ crystallization of bacterial cellulose II. Influences of different polymeric additives on the formation celluloses $I_\alpha$ and $1_\beta$ at the early stage of incubation," Cellulose, 1996, pp. 229-242, vol. 3.

\* cited by examiner

| Polymer Additive | Cellulose wt% | Polymer wt% | Water wt% |
|---|---|---|---|
| 1wt% PEO1 | 55±2 | 23±3 | 22±1 |
| 3wt% PEO1 | 40±3 | 46±4 | 14±2 |
| 5wt% PEO1 | 29±5 | 64±5 | 7±2 |
| 1wt% PEO6 | 66±2 | 26±2 | 9±1 |
| 3wt% PEO6 | 33±0 | 49±3 | 18±2 |

Fig. 7

| Polymer Additive | Melting Point (°C) |
|---|---|
| 1wt% PEO1 | 60.5±0.5 |
| 3wt% PEO1 | 61.4±2.4 |
| 5wt% PEO1 | 65.7±1.9 |
| Pure PEO1 | 68.2±0.5 |
| 1wt% PEO6 | 64.3±1.6 |
| 3wt% PEO6 | 71.4±3.1 |
| Pure PEO6 | 71.9±0.2 |

*Fig. 9*

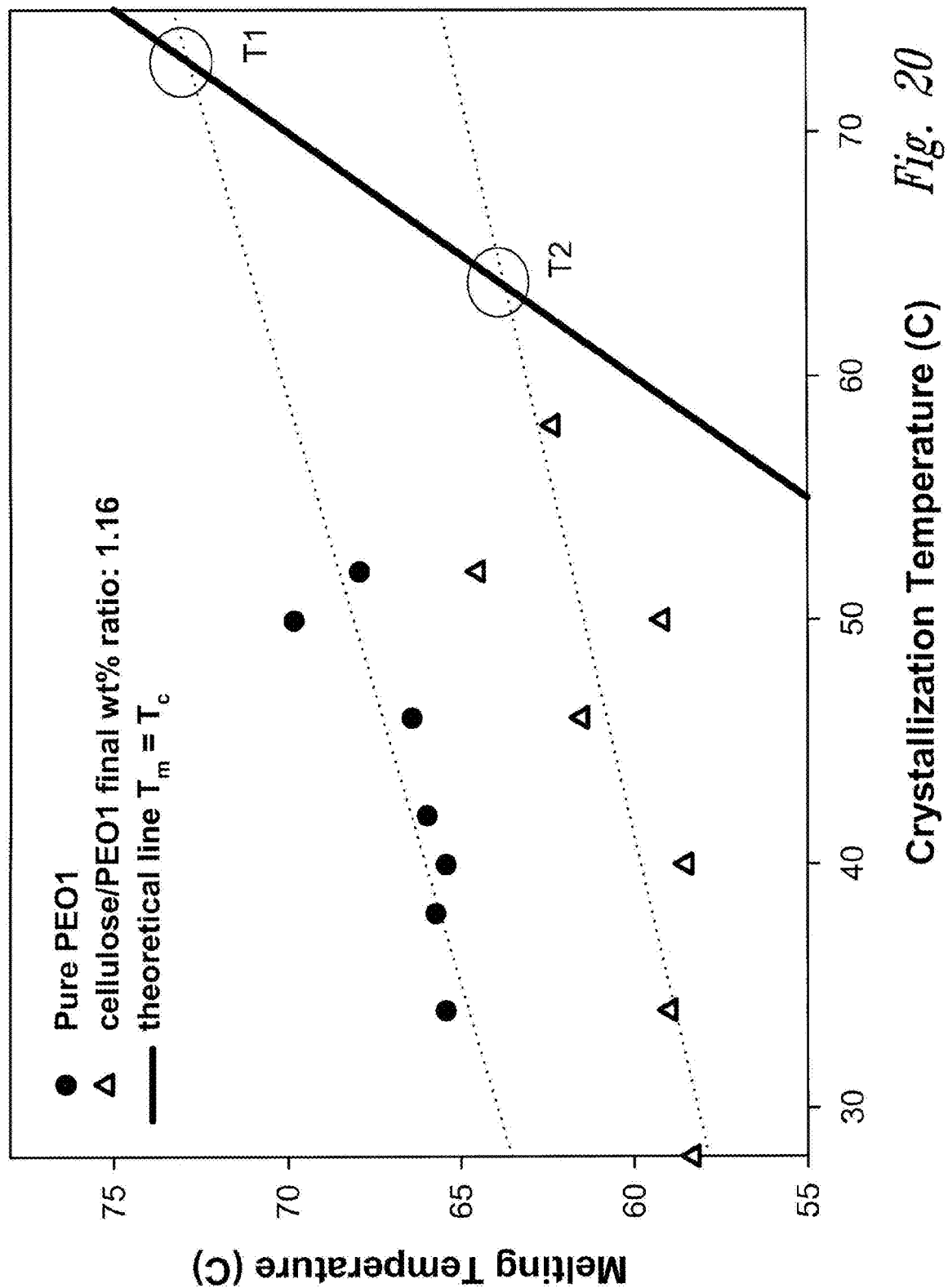

METHOD OF IN SITU BIOPRODUCTION AND COMPOSITION OF BACTERIAL CELLULOSE NANOCOMPOSITES

CROSS-REFERENCE TO RELATED APPLICATIONS

This application claims the benefit of priority to U.S. Provisional Application No. 60/957,279, filed 22 Aug. 2007, and entitled METHOD OF IN SITU BIOPRODUCTION AND COMPOSITION OF BACTERIAL CELLULOSE NANOCOMPOSITES, which is incorporated herein by reference in its entirety.

STATEMENT REGARDING FEDERALLY-SPONSORED RESEARCH

The invention was made with government support under 2003-34270-13389 awarded by USDA/CSREES. The government has certain rights in the invention.

FIELD OF THE INVENTION

Aspects described herein relate generally to bacterial cellulose and cellulose nanocomposite materials and films, and more particularly to in situ methods for biosynthesis of cellulose fibrils in a highly and uniformly dispersed polymer matrix material to provide for unique cellulose nanocomposite materials, the dispersed fibrils of which can be structurally 'tailored' by varying the growth medium and/or conditions.

BACKGROUND

Bacterial cellulose. Cellulose is the most abundant biopolymer on earth, synthesized by plants, fungi, algae, bacteria and some animals. Its chemical structure is a polymer composed of glucose monomers linked thru β-1,4. Most celluloses occur as a crystalline allomorph cellulose I, the native allomorph, which can be treated to form into other allomorphs such as cellulose II, III, IV synthetic products. Cellulose I is composed of both Iα and Iβ crystalline unit cells. Cellulose Iα is triclinic with dimensions a=6.3 Å, b=6.9 Å, c=10.36 Å, α=113.0°, β=121.1°, γ=76.0° (Vietor, 2000). Cellulose Iβ is monoclinic with dimensions a=8.17 Å, b=7.86 Å, c=10.38 Å and γ=97.0° (Brown, 1984). Morphologically, cellulose I exists as submicroscopic rods known as microfibrils, the shape and size of which vary and are governed by the genetics of the organisms that generate it. The most common source of cellulose is from higher plants such as cotton and ramie producing microfibril widths of 2-5 nm. Algal, bacterial and tunicate celluloses forms larger microfibrils of 15-30 nm in width and these celluloses are rich in Iα crystalline.

Bacterial cellulose is a product of microbial primary metabolism. For example, cellulose is produced by species such as *Zoogloea, Sarcina*, such as *Sarcina ventricula* (Canale-Parola1960), *Salmonella, Rhizobium* (Napoli, 1975), *Pseudomonas*, such as *Pseudomonas fluorescens* (Spiers, 2003), *Escherichia, Agrobacterium*, such *Agrobacterium tumefaciens* (Matthysse, 1995), *Aerobacter, Achromobacter, Azotobacter, Alcaligenes*, and *Acetobacter*, also known as *Gluconacetobacter*. The most studied and used cellulose-producing bacteria specie is *Acetobacter xylinum*, which includes the strains ATCC 23769, 10145, 53582, AX5 and many others (Brown, 1996) (Klemm, 20010. Microorganisms of *Acetobacter* are obligate aerobes and generally are found in fruits, in vegetables, most likely in rotting fruits and vegetables, in vinegar, fruit juices and alcoholic beverages (Klemm, 2001).

When a liquid medium, known as H-S medium (Hestrin, 1954) that consists of 2 wt % D-glucose, 0.5 wt % peptone, 0.5 wt % yeast extract, 0.27 wt % disodium phosphate, 0.115 wt % citric acid (monohydrate), and distilled water is inoculated with a strain of *Acetobacter xylinum*, a cellulose pellicle will be formed on the air-liquid medium interface. Glucose functions as bacteria's carbon source, peptone as nitrogen source, yeast extract as vitamin source and citric acid and disodium phosphate as buffer system for the medium. Before the medium is inoculated with a bacteria strain, it goes through sterilization by autoclaving. During this sterilization process, D-glucose is partially isomerized to D-fructose thus degrading to dark-yellow products resulting into a yellow liquid growth medium. About 6% of D-glucose will be lost due to transformation to fructose. To stabilize D-glucose and to minimize its loss, citric acid, which is part of the buffer system acts as a stabilizing agent. The mechanism of cellulose formation by *Acetobacter xylinum* is as follows; the bacteria increase their population by consuming glucose and oxygen initially dissolved in the liquid medium, when the oxygen has diminished, only bacteria having access to air can continue cellulose-producing activity, thus forming the cellulose pellicle at/in the air-liquid medium interface. The bacteria below the surface area are considered dormant but can be reactivated by using the liquid as an inoculum for a new culture medium. *A. xylinum* cells when fed with glucose cause a slow evolution of carbon dioxide as it forms cellulose. The gas accumulates on the surface of cellulose fibrils and is believed to be another cause of the cellulose pellicle flotation on the air-liquid interface. The increase of mass or thickness of cellulose pellicle occurs at the upper part of the pellicle surface, where oxygen is accessible. The cellulose polymers diffuse through the cellulose pellicle sheet to access the oxygen. The oldest part of the pellicle is the under part, which has been pushed progressively downwards into zones of decreasing oxygen pressure and lesser activity. The monosaccharide is converted by *Acetobacter xylinum* dehydrogenase into (keto)gluconic acids. D-glucose not only acts as a carbon source but also as a cellulose precursor.

Bacterial cellulose is potentially useful in many applications, but large-scale production of this material is yet to be developed. Static culture, which is a better production method requires wide (e.g. extended, substantial) surface area since the cellulose pellicles form at/in the air-liquid surface. However, highly extended (e.g., wide) culture surface areas are impractical and thus unsuitable for large-scale cultivation, and further improvements are needed to provide economical processes for bacterial cellulose production.

Numerous attempts have been made to increase production of bacterial cellulose, but none have yet proven feasible. Vandamme (Vandamme, 1998) and coworkers, for example ascertained that improvement of bacterial cellulose production could be achieved by proper strain selection, mutation, medium composition optimization, and physico-chemical fermentation parameter control. These authors combined nutritional, genetic and bioprocess-technological optimization in attempts to obtain high levels of cellulose production, and with agitated culture demonstrated that cellulose formation is enhanced by adding insoluble microparticles such diatomaceous earth, silica, small glass beads and loam particles. Another way of enhancing production in agitated culture is by adding ethanol, since ethanol is metabolized during the growth cycle of *Acetobacter*, producing more cellulose as transformation of glucose to fructose is inhibited. Jonas and coworkers' (Jonas, 1998) extend the Vandamme methods by using pH control to improve production, finding an optimal pH range of 4 to 7. One method of pH control, for example, is by using HCl and NaOH as described by Hestrin and Schramm (Hestrin, 1954). There is also an optimal temperature for cellulose production by *Acetobacter* strains, the range lying between 20° C. to 30° C. Most authors use 28-30° C. (Vandamme, 1998). In 1963, Webb and Colvin (Webb, 1963) added plant extracts from a number of plant sources resulting in increased cellulose synthesis by *A. xylinum*. The plant extracts were from tomatoes, carrots, potatoes, oranges and spinach leaves. Addition of endo-1,4-glucanase from *Bacillus subtilis* also enhanced bacterial cellulose production. When glucanase was added, the structural properties of the bacterial cellulose were not modified (Tanouchi, 1995). Joseph (Joseph, 2003) used polyacrylamide-co-acrylic acid to enhance bacterial cellulose production in shake culture, but the morphology of the product was changed when compared to the native product. Static culture is the most common method to grow bacterial cellulose. Aside from shaking or agitating cultures, bacterial cellulose can also be produced using an airlift reactor equipped with draft tube and riser; or using a rotating disk reactor where part of the surface of the disk is alternately positioned between the liquid medium and the atmosphere (Shoda, 2005).

Bacterial cellulose is primarily composed of Iα crystalline forms with relatively small amounts of Iβ present. *Acetobacter* cellulose, for example, is estimated to consist of about 60% to 70% Iα, which is very different from cotton cellulose that comprises 60% to 70% Iβ (Atalla, 1984). The presence of stress during the development of cellulose is believed to cause the formation of the Iα crystalline form. In crystallization of Japanese cypress tracheid cellulose, the stress is frequently exerted by the growing cells which stretch the primary cell wall of the plant examined. Iβ phase forms when the stress is relieved due to the fluidity of the environment thereby result in the presence of both Iα and Iβ phases in the tracheid cellulose (Kataoka, 1999). The ratio of Iα and Iβ can be determined using FT-IR spectra, where a peak at 750 cm-1 represents Iα, and a peak at 710 cm-1 represents Iβ (Id).

Physical properties of bacterial cellulose can be modified in many ways. When hemicellulose-like saccharides are added into the liquid medium growth of bacterial cellulose, its microfibril aggregation patterns are modified, whereby Iα-type crystalline arrangements transform to Iβ crystalline type. Thus, hemicellulose addition appears to transform bacterial cellulose to the higher plant cellulose structure (Uhlin, 1995). A drying process can alter the degree of crystallinity of cellulose but will not change Iα/Iβ ratio (Udhardt, 2005). Isolation procedures may also have an effect on the structure of bacterial cellulose (Uhlin 1995).

Bacterial cellulose is an excellent alternative to plant cellulose, particularly in areas where plant cellulose can't be used, such as where a high purity crystalline cellulose structure is essential. Table 1, for example, lists some of the patented cellulose products and applications (e.g., in the health care sector where its biocompatibility is recognized). 'Never-dried' bacterial cellulose has been demonstrated to have suitable biocompatibility for use in wound healing (Czaja, 2006). Additional known uses include stereo headphone diaphragms, food, paper, chromatographic techniques, cosmetics stabilizer and for latex binders. Another application is in membrane technology as BC has highly porous feature. The major utilization of BC is in biomedical or health sector. The unique nanostructure of bacterial cellulose gives it a high mechanical strength and remarkable physical properties in wet and dry state thus making this material very functional in many applications. However, although significant applications have been realized, mass production has not been viable.

TABLE 1

Art recognized cellulose products and applications thereof.

| Cellulose Product | Uses and Application |
|---|---|
| Temporary artificial skin (Biofill ®, Bioprocess ®, Gengiflex ® (Biofill01) [Biofill02] | Treatment for burns, ulcers and dental implants |
| Nonwoven paper or fabric (Weyerhaeuser), [Biopolymer] | Enhance the property of latex or binders, repair old documents |
| Diaphragms (Cannon, 1991) | Stereo headphones |
| Microbial cellulose (MC_patent) | Immobilization of proteins, chromatographic techniques Food, food or diet fiber substitute Stabilizer, viscosity modifiers |
| BASYC (Klemm, 2001) | Artificial blood vessels for microsurgery Protective cover for micronerve structure |
| Membranes (Choi, 2004) | Environmentally compatible ion-exchange membrane |

Nanocomposites. Nanocomposites are a new class of composites characterized by ultra fine phase dimensions of 1 nm to 1000 nm. Such nanocomposites include hybrid materials comprising polymer matrix reinforced with a nanoscale reinforcement (e.g., fibers or platelets). There are three main classifications of nanocomposites reinforcements: (i) nanoscale level in three dimensions such as spherical silica; (ii) elongated reinforcements with nanoscale level in two dimensions such as fibers and carbon nanotubes (iii) sheet-like structures with nanoscale level in one dimension such as layered silicates, mica and clay.

The outstanding properties of bacterial cellulose that make it excellent as a reinforcing material for nanocomposites include but are not limited to: high purity, without the blend of lignin and other hemicellulose as with plant; high crystallinity; biodegrability; water holding capacity up to 100-times its weight; and excellent biological affinity. The reinforcing effect of cellulose comes from its 'whiskers' percolating network and good interfacial compatibility with the polymer matrix. When the cellulose and its polymer matrix do not have a good interaction or good miscibility, the nanocomposite is likely to possess inefficient mechanical and physical properties. Interactions of the polymer matrix with cellulose are closely associated with the following factors: solubility of polymer additives, diffusibility of the additives to each microfibril surface and the extent of hydrogen bonding between the additives and microfibrils. Designation of a polymer for cellulose nanocomposite involves determination or estimation of the interfacial compatibility between polymers based qualitative considerations, and thus description of precise atomistic scale interfacial phenomena is difficult to assess. Currently, the choice of the polymer matrix is typically based primarily on trial and error. One of the properties of a material that can give an approximation of its behavior when interacting with another material to form into a nanocomposite is the solubility parameter ($\delta$). Addition of polymers that have solubility parameters close to cellulose can affect cellulose aggregation. There are numerous existing approaches of determining the solubility parameter ($\delta$). For example, one approach is to use functional group contributions of a material or a polymer (VanKrevelen, 1976). The solubility parameter for cellulose was evaluated by Bochek (Bochek, 1993), who obtained 56.2 $(J/cm^3)^{1/2}$. When compared to the δ values calculated using other methods, Bochek's evaluation is greater, based on taking into account the highly polar characteristic of cellulose, where the polar characteristics are the number of hydrogen bonds and their energies. The values of cellulose δ acquired from other methods are (method: δ): Small: 21.0 (Small, 1953), Hoy: 29.6 (Hoy, 1970), Van-Krevelen: 38.8 (VanKrevelen, 1976), Fedors: 34.9 (Fedors, 1974), all δ are in units $(J/cm^3)^{1/2}$.

*Acetobacter* synthesized bacterial cellulose has been grown in static culture the presence of limited amounts of particular polymers to study details of microfibril formation (aggregation) and crystallization, or understand the functionality of cellulose in plants. The polymers used include hemicellulose (Uhlin, 1995) (Yamamoto, 1994) (Haigler, 1982), Calcofluor (Haigler, 1980), Calcofluor White or Congo Red dyes (Colvin, 1983), xylan (Yamamoto, 1996) (Yamamoto, 1994) (Ohad, 1963), phosphomannan (Ohad, 1963), xyloglucan (Whitney, 19990 (astley 2003), pectin (Astley, 2003) (Ohad, 1963), glucomannan and galactomannan (Whitney, 1998), etc. The aggregation of bacterial-produced subfibrils has been shown to be altered in the presence of particular agents. For example, bacterial cellulose synthesized in the presence of the fluorescent brightener Calcofluor under static pellicle culture conditions (Haigler, 1980), indicates that Calcofluor prevents the assembly of crystalline cellulose microfibrils and ribbons by *Acetobacter zylinum*, where Calcofluor alters cellulose crystallization by hydrogen bonding with glucan chains. Bacterial cellulose has been synthesized in the presence of hemicellulose under static pellicle culture conditions (Uhlin, 1995, Yamamoto, 1994, Haigler, 1982), where patterns of aggregation of the bacterial cellulose were modified to be more like the plant Iβ-type than the bacterial Iα-type when the cellulose was produced in the presence of hemicellulose-like saccharides (xyloglucan; mannan, xylan and carboxymethyl celluose). Other polymers studied include: dyes (Colvin, 1983), xylan (Yamamoto, 1996) (Yamamoto, 1994) (Ohad, 1963); phosphomannan (Ohad, 1963), xyloglucan (whitney 1999) (Astley 2003); pectin (Astley 2003) (Ohad 1963); and glucomannan and galactomannan were added to the growth medium of BC-producing bacterium, forming thinner diameter cellulose ribbons (Whitney, 1998). These studies, however teach nothing about the distribution or properties of cellulose fibrils compositions comprising such particular polymers.

SUMMARY OF THE INVENTION

A novel process for in situ bioproduction of bacterial cellulose nanocomposites is described herein. As widely appreciated in the art, one of the problems in making cellulose nanocomposites is the difficulty in dispersing the nanofibers into the polymer matrix, and various researchers have attempted mechanical and chemical treatments such as the use of shear or surfactants, but have met with limited success.

Certain aspects relate to cellulose-based nanocomposites having biodegradability, biocompatibility and improved mechanical properties, formable via molding processes, and to methods of producing the same.

In particular aspects of the present invention the production step of the nanofibers is integrated with the dispersion step in order to make the nanocomposites; that is, instead of first making the nanofibers (for instance by hydrolysis of tunicin or plant cellulose) and then attempting to disperse it in a polymer matrix, the cellulose nanofibers are directly synthesized in situ within the polymer matrix. In certain aspects, this is accomplished by forcing the cellulose-producing bacteria to synthesize the cellulose chains into a polymer-rich medium where the growing cellulose directly mixes with the polymer as it is being synthesized by the bacteria. The resulting cellulose/polymer composition comprises a good mix/dispersion of the two components. In addition to improving the dispersion of the cellulose into the matrix, this in situ bioproduction of nanocomposites allows for controlling the size, crystallinity and morphology of the cellulose fibers.

Aspects of the present invention, therefore, relate to novel bacterial cellulose-based nanocomposites having improved, tailored mechanical properties and also to novel methods of producing said nanocomposites.

In particular aspects, the composition of the final product is controlled by varying the concentration of the polymer in the medium to obtain novel nanocomposites with tailored composition and fiber dimensions.

The nanocomposite compositions have many uses including but not limited to those listed in Table 1, wound healing dressings and materials, stereo headphone diaphragms, food, paper, chromatographic techniques, cosmetics stabilizers, binders, membrane technology (BC has highly porous feature), etc. Preferred uses are those related to biomedical or health sector implementations, as discuss herein and as recognized in the art in relation to existing BC and nanocomposite uses.

Particular aspects provide a method for making a dispersed cellulose nanocomposite in situ, comprising: providing a growth medium comprising an amount of at least one polymer matrix material, the medium suitable for growth of cellulose-producing microbial or plant cells; and incubating the growth medium with the cells under conditions suitable to provide for in situ biosynthesis and concurrent dispersion of the fibrils in the medium and polymer matrix material to provide a cellulose nanocomposite material or film having a polymer content and in which the cellulose fibrils are at least one of dispersed, highly dispersed and uniformly dispersed, and wherein at least one of cellulose fibril structure and composition of the nanocomposite material is determined, at least in part, by the amount or nature of the at least one polymer matrix material. In certain embodiments, determination of fibril structure comprises determination of at least one of fibril length, fibril diameter and fibril aspect ratio. Certain aspects further comprise removing or separating the cellulose nanocomposite material or film from the medium, and/or further comprise washing the cellulose nanocomposite material or film to remove residual medium. Certain embodiment further comprise freeze-drying the cellulose nanocomposite material or film, and/or further comprise forming a molded product using the cellulose nanocomposite material or film. In particular embodiments, the polymer matrix material is present in an amount between about 1 wt % and about 10 wt % of the growth medium, and the polymer component of the cellulose nanocomposite material comprises from about 10 wt % to about 80 wt % of the produced cellulose nanocomposite material. In certain aspects, the cellulose nanofiber diameter is between about 30 nm to about 130 nm, and the cellulose nanofibers are highly dispersed and uniformly dispersed within the composite. In particular aspects, the in situ synthesized cellulose comprises at least one of bacterial cellulose and plant cellulose. In particular aspects, the cellulose comprises bacterial cellulose, and in certain embodiments, particularly the bacterial cellulose is that produced by *Acetobacter xylinum*. In particular aspects, the polymer matrix material comprises at least one of a biobased polymer, a plant-derived polymer, a synthetic polymer and a thermoplastic polymer. In certain embodiments, the polymer matrix material comprises at least one selected from the group consisting of carboxymethyl cellulose (CMC), polyethylene oxide (PEO), polyvinyl alcohol (PVA), polybutadiene, poly-lactic acid (PLA), polyhydroxy alkanoates (PHAs), polyvinyl acetate, polyamides, nylons, polyacrylic acid (PAA), polypropylene, poly(ethylene-co-vinyl acetate) (EVA), poly (diallydimethylammonium chloride) (PDDA), starch, acrylic resins, styrene-butyl acetate, Xylan, chitosan, poly(B-sydroxyoctanoate) (PHO), hemicellulose, phosphomannan, glucomannan, galactomannan, xyloglucan, and pectin. In particular aspects, the polymer matrix material comprises at least one of polyethylene oxide (PEO) and polyvinyl alcohol (PVA), and in certain embodiments, the polymer matrix material comprises polyethylene oxide (PEO). In particular aspects, the growth medium comprises at least one of D-glucose, peptone, yeast extract, sodium diphosphate and citric (citric acid and/or citrate).

Additional aspects provide an in situ dispersed cellulose nanocomposite material formed by the inventive methods. In certain aspects, the in situ dispersed cellulose nanocomposite material comprises a formed, shaped or molded product comprising in situ dispersed cellulose nanocomposite material. In particular embodiments, the in situ dispersed cellulose nanocomposite material comprises at least one of a biobased polymer, a plant-derived polymer, a synthetic polymer and a thermoplastic polymer. In certain aspects, the in situ dispersed cellulose nanocomposite material comprises at least one selected from the group consisting of carboxymethyl cellulose (CMC), polyethylene oxide (PEO), polyvinyl alcohol (PVA), polybutadiene, poly-lactic acid (PLA), polyhydroxy alkanoates (PHAs), polyvinyl acetate, polyamides, nylons, polyacrylic acid (PAA), polypropylene, poly(ethylene-co-vinyl acetate) (EVA), poly(diallydimethylammonium chloride) (PDDA), starch, acrylic resins, styrene-butyl acetate, Xylan, chitosan, poly(B-sydroxyoctanoate)(PHO), hemicellulose, phosphomannan, glucomannan, galactomannan, xyloglucan, and pectin.

BRIEF DESCRIPTION OF THE DRAWINGS

FIG. 7 shows, according to exemplary aspects, TGA (Thermal Gravimetric Analysis) approximation of chemical compositions of nanocomposites.

FIG. 9 shows, according to exemplary aspects, DSC data of PEO1 and PEO1/cellulose nanocomposites.

FIG. 20 shows, according to exemplary aspects, equilibrium melting points obtained for pure PEO1 and nanocomposite of cellulose/PEO1 final wt % ratio 1.16.

DETAILED DESCRIPTION OF THE INVENTION

Figure 1:
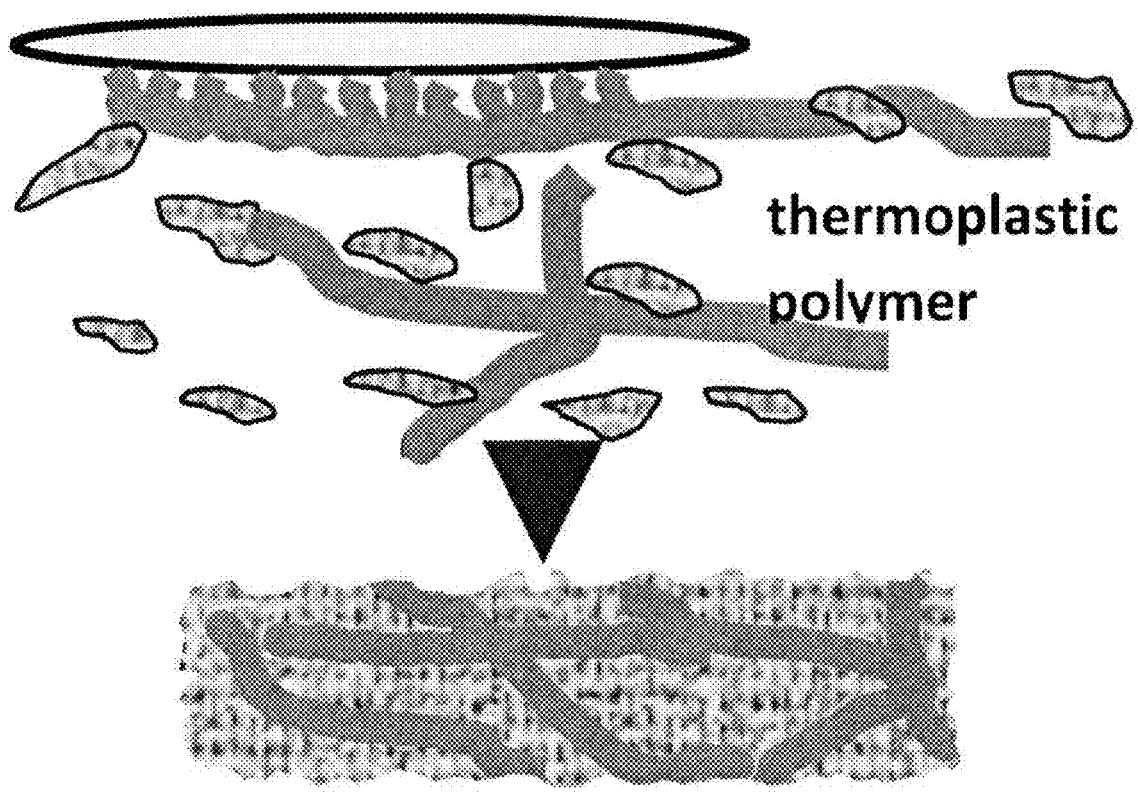
FIG. 1 illustrates in situ growth development of bacterial cellulose nanocomposites according to exemplary aspects of the present invention.

Particular aspects provide novel material compositions of bacterial cellulose nanocomposites, and procedures for in situ bioproduction of the bacterial cellulose nanocomposites. Certain aspects provide bacterial cellulose and cellulose nanocomposite materials and films, and in situ methods for biosynthesis of cellulose fibrils in a highly and uniformly dispersed polymer matrix material to provide for unique cellulose nanocomposite materials, the dispersed fibrils of which can be structurally 'tailored' by varying the growth medium and/or conditions (e.g., polymer wt %).

Certain composition embodiments comprise materials that mimic the natural mechanical properties of a given biological structures, such as veins, arteries, valves, organs and other related structures, where the material have strong biocompatibility and biodegradation properties.

Preferred embodiments of the present invention include methods to produce nanocomposites of biocompatible materials, wherein the material composition can be optimized by the incorporation of nanofibers, ranging in size and distribution.

Exemplary implementations of this invention include biomaterials for implantable devices and structures, biocompatible tools, stents, artificial veins, arteries, valves, organs and other related structures.

Other exemplary embodiments comprise biocompatible and biodegradable materials for consumer packaging, food packaging, and other consumer products.

"Nanocomposite" as used herein in particular embodiments refers to an oligomer, polymer or copolymer having dispersed therein a plurality of individual platelets obtained from an Exfoliated, Intercalated Layered Material.

"Matrix Polymer" as used herein in particular embodiments refers to a thermoplastic or thermosetting polymer in which the exfoliate is dispersed to form a nanocomposite. According to particular aspects, essentially any plastic polymer that has some degree of miscibility/interactions with cellulose and is water soluble can be used, and combinations of such polymer materials can be used. In other exemplary embodiments polymer matrix materials include but are not limited to biobased polymers, a plant-derived polymers, synthetic polymers, thermoplastic polymers, carboxymethyl cellulose, polyethylene oxide (PEO), polyvinyl alcohol (PVA), polybutadiene, poly-lactic acid (PLA), polyhydroxy alkanoates (PHAs), polyvinyl acetate, polyamides, and nylons.

"Intercalant Polymer" or "Intercalant" as used herein in particular embodiments refers to an oligomer or polymer that is sorbed between Platelets of the Layered Material to form an Intercalant.

In chemistry, in situ typically means "in the reaction mixture."

Particular aspects provide a method for making a cellulose nanocomposite, comprising biosynthesis of cellulose fibrils in situ using a growth medium comprising a polymer matrix material, under conditions suitable to provide for dispersion of the fibril in situ biosynthesis throughout the growth medium as the fibrils are being formed to provide a cellulose nanocomposite material or film wherein the cellulose fibrils are highly or uniformly dispersed in the cellulose nanocomposite material. In certain aspects, the method further comprises removing or separating the cellulose nanocomposite material or film from the medium. In certain aspects, the method further comprises washing the cellulose nanocomposite material or film to remove residual medium. In certain aspects, the method further comprises freeze-drying the cellulose nanocomposite material or film. In certain aspects, the method further comprises forming a molded product using the cellulose nanocomposite material or film. In particular implementations of the methods, the polymer additive is between about 1 wt % and 10 wt % of the growth medium, and the polymer component of the cellulose nanocomposite material is present from about 10 wt % to about 80 wt %. In certain embodiments, the cellulose nanofiber diameter is between about 30 nm to about 130 nm, and the cellulose nanofibers are dispersed or uniformly dispersed within the composite. In particular aspects, the cellulose comprises at least one of bacterial cellulose and plant cellulose. In preferred aspects, the cellulose comprises bacterial cellulose. In particularly preferred aspects, the bacterial cellulose is that produced by *Acetobacter xylinum*. In certain embodiments, the polymer matrix material comprises a biobased polymer, a plant-derived polymer, a synthetic polymer, or a thermoplastic polymer. In certain aspects, the polymer matrix material comprises at least one selected from the group consisting of carboxymethyl cellulose (CMC), polyethylene oxide (PEO), polyvinyl alcohol (PVA), polybutadiene, poly-lactic acid (PLA), polyhydroxy alkanoates (PHAs), polyvinyl acetate, polyamides, nylons, polyacrylic acid (PAA), polypropylene, poly(ethylene-co-vinyl acetate) (EVA), poly(diallydimethylammonium chloride) (PDDA), starch, acrylic resins, styrene-butyl acetate, Xylan, chitosan, poly(B-sydroxyoctanoate) (PHO), hemicellulose, phosphomannan, glucomannan, galactomannan, xyloglucan, and pectin. Preferably, the polymer matrix material comprises polyethylene oxide (PEO) or polyvinyl alcohol (PVA). More preferably, the polymer matrix material comprises polyethylene oxide (PEO). In certain implementations, the growth medium comprises at least one of D-glucose, peptone, yeast extract, sodium diphosphate and citric (citric acid and/or citrate).

Additional embodiments provide a cellulose nanocomposite material formed by any of the methods disclosed herein. In certain aspects the cellulose nanocomposite material comprises a molded product.

Specific manifestations and Examples of the invention are provided herein as illustrations, and are not intended to limit the scope of the invention, as various modifications will become apparent to one skilled in the art.

Example 1

Exemplary Process for In Situ Bioproduction of Bacterial Cellulose Nanocomposites Methods:

A process for in situ bioproduction of bacterial cellulose nanocomposites, comprising:

(i) dissolving D-glucose, peptone, yeast extract, sodium diphosphate and citric in distilled water, together with a polymer matrix additive to provide the medium, where the nanocomposite may comprise a biobased or synthetic polymer matrix such as a cellulose derivative or a thermoplastic polymer (polybutadiene, polyethylene oxide, polyvinyl alcohol);

(ii) autoclaving the medium (e.g., at 121° C. for 15 minutes);

(iii) cooling the medium (e.g., to room temperature), and inoculating the medium with a suitable cellulose-producing bacterial strain (e.g., a *Acetobacter xylinum* strain) or with a suspensions taken from a grown cellulose pellicle;

(iv) incubating the inoculated medium at a suitable growth temperature (e.g, at a temperature of about 29° C.) with stirring (e.g., with mild stirring using a stirring plate and a magnetic stirrer) until the nanocomposite film forms at the air-liquid interface; and (v) removing or separating the nanocomposite material from the medium, washing the nanocomposite material with distilled water, and freeze-drying the material.

Particular aspects comprise an additional step (vi) comprising molding the samples using one or more compression molding processes Results:

According to preferred aspects of the present invention, characterization of the resulting nanocomposite material not only indicates that the cellulose nanofibers are better dispersed in the polymer matrix, but also that they have different morphologies when grown in situ into the polymer solution, and the nanocomposite compositions can be manipulated by varying the polymer concentration of the solution. For example, with a medium that has 1 to 4% polyethylene oxide (PEO), cellulose/nanocomposites with 30 to 70% wt PEO were obtained and the cellulose nanofiber was reduced from about 130 nm diameter to about 30 nm.

According to particular aspects, therefore, cellulose nanocomposites can be produced, where the cellulose morphology is tailored by in situ growing of bacterial cellulose into a thermoplastic polymer solution.

Example 2

Growth Development of Bacterial Cellulose Nanocomposites

Polymer was added to the Hestrin-Schramm1 liquid medium of cellulose-producing bacterium *Acetobacter xylinum* strain #23769 grown in magnetically-stirred environment, as illustrated in FIG. 1. Polymers chosen were:

PEO(poly(ethylene oxide))

$PEO1(MW=100,000)$ $PEO6(MW=600,000)$

PVA(poly(vinyl alcohol))

$PVA22(MW=22,000)$ $PVA88(MW=88,000)$ $CMC$(carboxymethyl cellulose)$CMC12(DP=1100\ DS=0.7)$ $CMC13(DP=400\ DS=0.7$ $CMC15(DP=1100\ DS=1.2)$

Example 3

Figure 2:
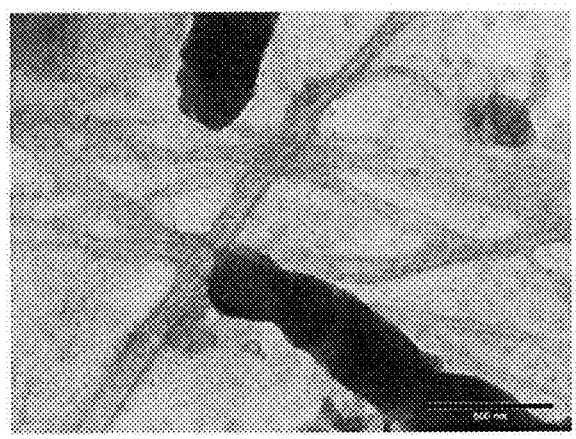
FIG. 2 shows, according to exemplary aspects, pure cellulose (fibril diameter: 75 nm±23 nm).
Figure 3:
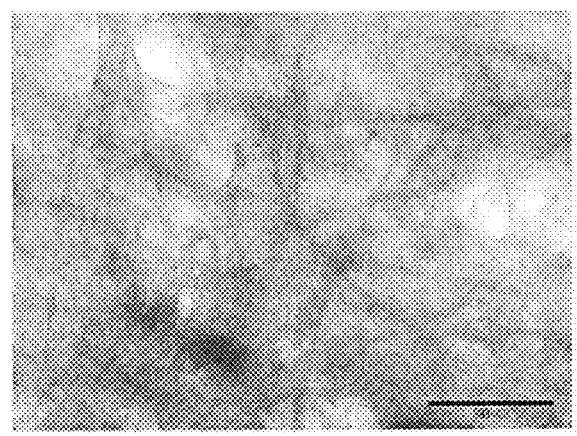
FIG. 3 shows, according to exemplary aspects, nanocomposite grown in medium with 1 wt % PEO1 (Fibril diameter: 28 nm±5 nm).
Figure 4:
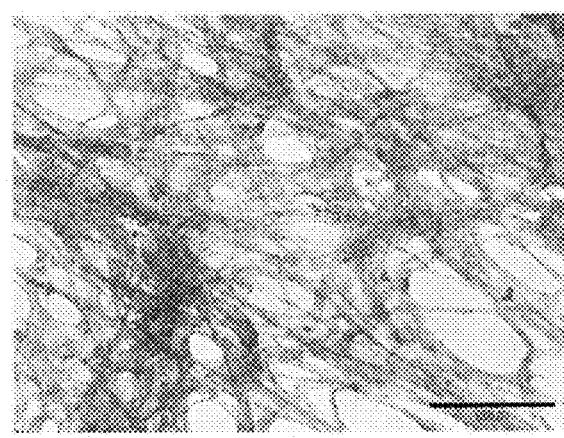
FIG. 4 shows, according to exemplary aspects, nanocomposite grown in medium with 3 wt % PEO1 (fibril diameter: 34 nm±5 nm).
Figure 5A:
FIGS. 5 A-D show, according to exemplary aspects, AFM- A) without polymer; B) with 1 wt % PEO1; C) with 3 wt % PEO1; and D) with 5 wt % PEO1.
Figure 5B:
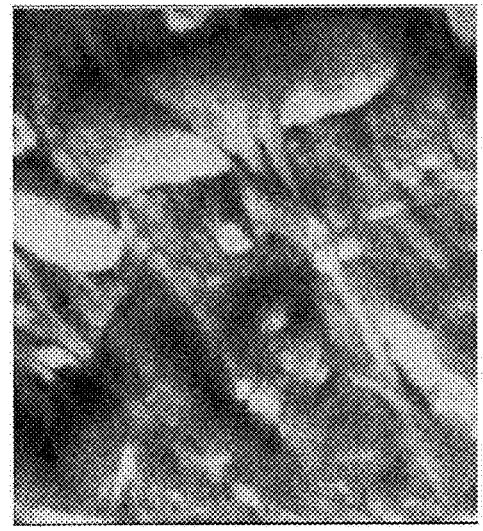
Figure 5C:
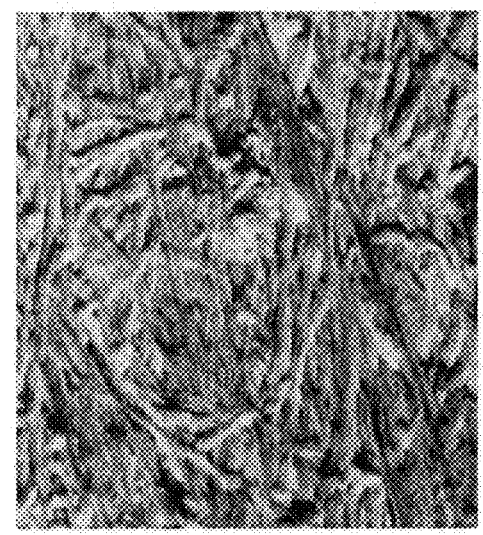
Figure 5D:
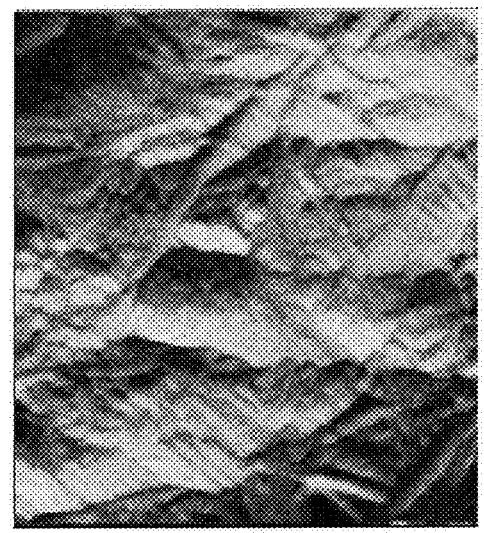

Morphology of nanocomposites when wet was characterized using TEM (Transmission Electron Microscope). Aspect ratios (L/d) of microfibrils are higher when PEO1 is present in the medium. See FIGS. 2, 3 and 4.

Example 4

AFM (Atomic Force Microscopy) was used to characterize the surface morphology of dried cellulose and PEO1/cellulose nanocomposites grown in culture medium. AFM imaging is shown in FIG. 5 of the following media: A) without polymer; B) with 1 wt % PEO1; C) with 3 wt % PEO1 and D) with 5 wt % PEO1.

Example 5

Figure 6:
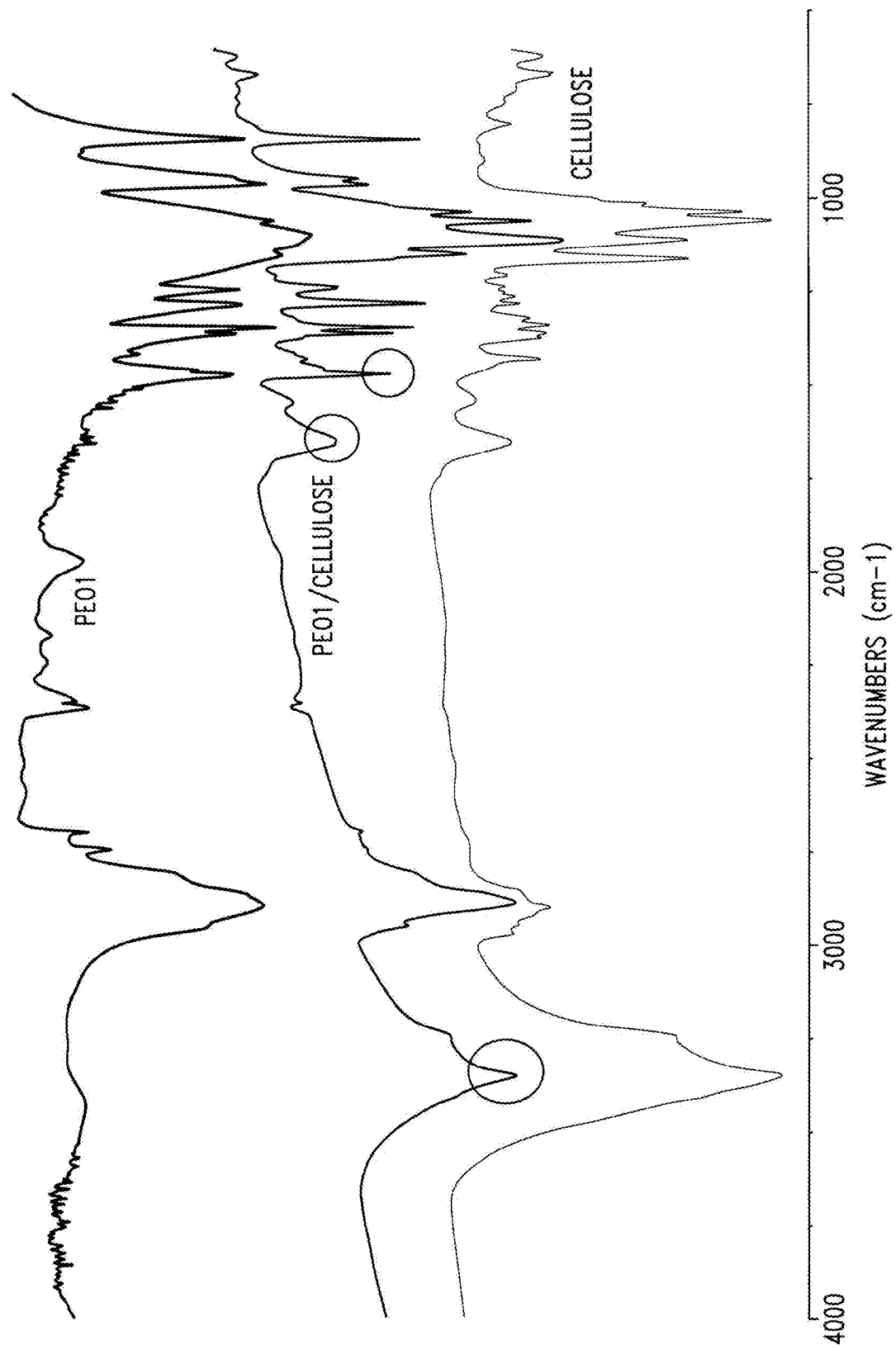
FIG. 6 shows, according to exemplary aspects, FT-IR (Fourier Transform Infrared) Spectroscopy of nanocomposites grown in medium with 3 wt % PEO1.

FT-IR (Fourier Transform Infrared Spectroscopy) was used to look at nanocomposites grown in medium with 3 wt % PEO1 (FIG. 6). Significant peaks appear in the grown product, in both pure cellulose and PEO; thus confirming the nanocomposites formation. No new peaks appeared, showing no chemical reaction denoting the formation of a blend.

Example 6

TGA (Thermal Gravimetric Analysis) provides approximations of chemical compositions of the nanocomposites. This study determined weight percentages of components in the nanocomposites, as shown in FIG. 7. As PEO additive increased, its composition in the nanocomposites increased.

Example 7

Figure 8:
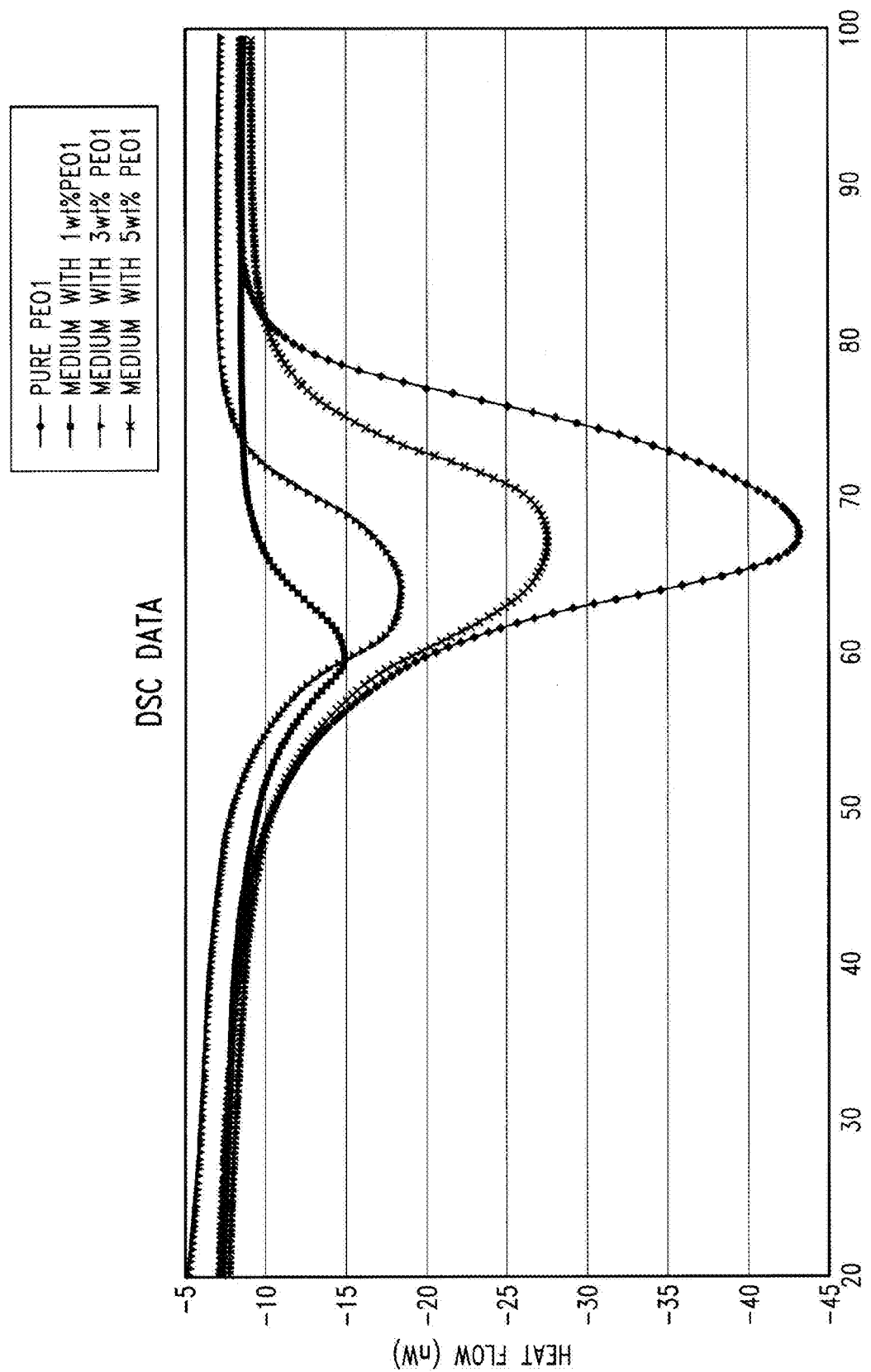
FIG. 8 shows, according to exemplary aspects, DSC (Dynamic Scanning Calorimetry) providing $T_g$ and $T_m$ of nanocomposites.
Figure 10A:
FIGS. 10 A-D show, according to exemplary aspects, TEM images of bacterial cellulose. a) cellulose grown without PEO, b) cellulose grown with 1 wt % initial PEO1 (1.16), c) cellulose grown with 3 wt % initial PEO1 (0.30), d) cellulose grown with 5 wt % initial PEO1 (0.17). Values in parentheses are cellulose/PEO1 final wt % ratio. Images were taken at 60K magnification.
Figure 10B:
Figure 10C:
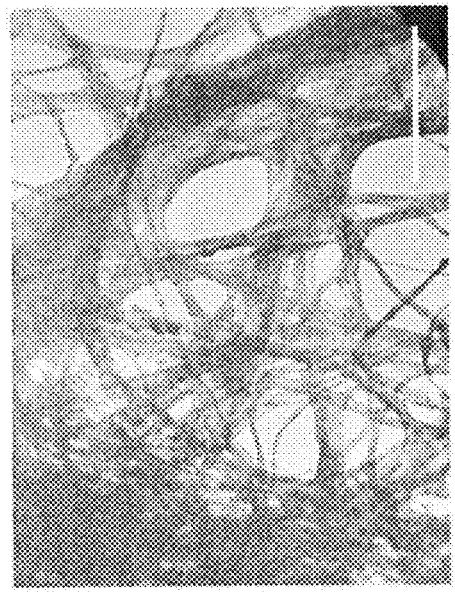
Figure 10D:
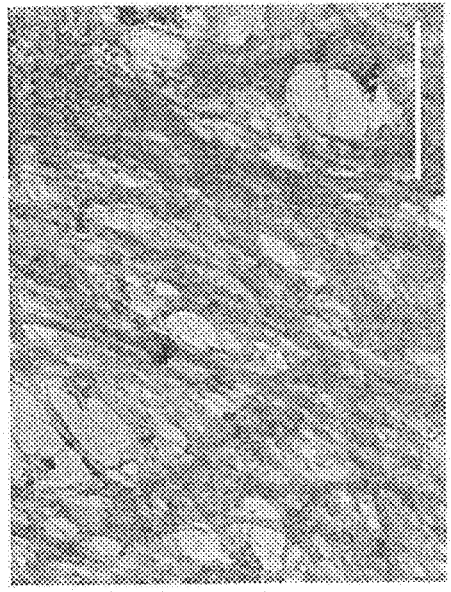
Figure 11A:
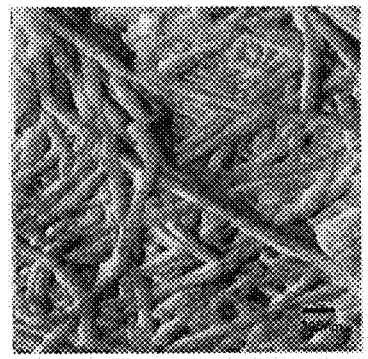
FIGS. 11 A-E show, according to exemplary aspects, AFM images of dried bacterial cellulose nanocomposites. Cellulose/PEO1 final wt % ratio: a) pure cellulose, b) 1.16, c) 0.40, d) 0.30, e) 0.17. Images were 2 µm×2 µm.
Figure 11B:
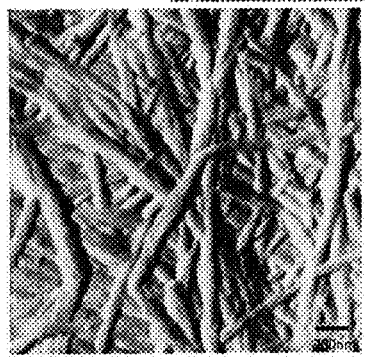
Figure 11C:
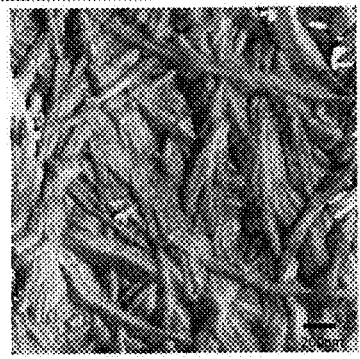
Figure 11D:
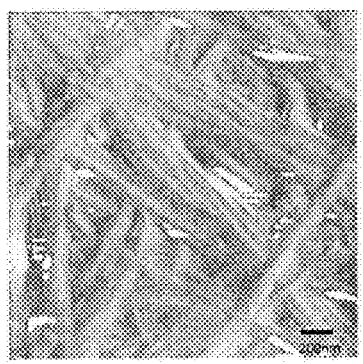
Figure 11E:
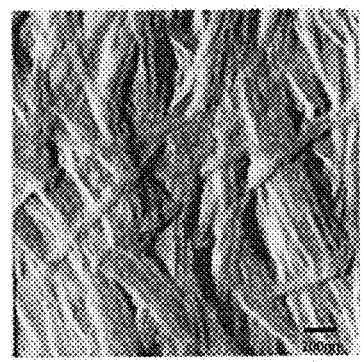

DSC (Dynamic Scanning Calorimetry) provides $T_g$ and $T_m$ of the nanocomposites. The minimum peaks shown in FIG. 8 denote the melting points of the samples listed in the [Polymer Additive/Melting Point] table in FIG. 9. This shows an interaction between PEO1 and cellulose as affirmed by the melting point depression.

Example 8

Bacterial Cellulose/PEO Nanocomposite Paper

Example Overview. There are many applications of bacterial cellulose (BC), including but not limited to stereo headphone diaphragms, food, paper, chromatographic techniques, cosmetics stabilizer latex binders, membrane technology (as BC has highly porous feature), biomedical or health sector uses. Most of these applications use pure BC and thus there is little flexibility in designing of properties. However, the diverse applications of BC demand diverse properties and according to aspects of the present invention, one way of altering BC properties is to grow it in situ under dispersion conditions with another polymer to form cellulose nanocomposites. BC, when grown in situ in dispersed liquid medium comprising other polymers seems to has altered morphology and properties when compared to corresponding native BC structures.

Nanocomposites are a relatively new class of composites characterized by ultrafine phase dimensions of 1 to 1000 nm. Cellulose nanocomposites are hybrid materials comprising a polymer matrix reinforced with nanoscale reinforcement such as fibrils or platelets. In composite science, the main requirements for efficient reinforcement are; large aspect ratio, good dispersion and interfacial stress transfer (Coleman, 2006). Adequate dispersion is a long-standing problem in the nanocomposite art, and with respect to composites in general. Fibers used for composites made by molding injections can clog the machinery because of the fiber aggregation. The high-energy surface of diminutive materials caused the difficulties of dispersion of the fibers.

BC by *Acetobacter xylinum* is produced from linear glucan chains and aggregates to form into cellulose ribbons (Brown, 1996). According to aspects of the present invention, the fact that BC starts with the linear glucan chains is beneficial since the polymer can be added to the liquid medium and thus can interact with the discrete fibrils before it can aggregate further into thick ribbons thus solving the dispersion problem. The BC and the polymer can then crystallize collectively forming into a nanocomposite. According to particular aspects, the biogenesis of BC is altered when growth medium of the BC-producing bacterium is altered, and the nanocomposites produced have correspondingly varied fibril dimensions, interfacial interactions and compositions. Therefore, according to preferred aspects, engineered nanocomposites for diverse applications are fabricated by varying the growth condition of the cellulose-producing bacterium according to the novel disclosed methods.

According to particular aspects, BC/polymer nanocomposites with tailored properties as well as nanocomposites with well-dispersed reinforcing fibrils are manufactured by adding the host polymer into the growth medium of *Acetobacter xylinum* under dispersion conditions. For example, the nanocomposite is formed by growing BC in the liquid medium with the host polymer in the magnetically-stirred environment. Stirring is applied to allow the host polymer to continuously be distributed in the medium since static environment will cause the polymer to accumulate in the bottom of the medium container. This is a novel process in fabrication of BC nanocomposites. Preferably, the well-characterized cellulose production of *Acetobacter xylinum* is used.

In particular preferred aspects, the polymer used is poly(ethylene oxide) (PEO), a polymer with several uses in medical applications. In this Example, characterization of the nanocomposites was performed using various instruments to illustrate exemplary attainable variations in properties. AFM and TEM were used to look at the physical dispersion of the cellulose fibrils in dry and wet states. TGA and FT-IR were employed to estimate the chemical compositions and molecular arrangements of components in nanocomposites. Finally, DMA and DSC were used to determine the mechanical and thermal properties.

Methods and Materials

Production

Starter Culture. *Acetobacter xylinum* strain 23769 purchased from ATCC was used to produce bacterial cellulose. Hestrin-Schramm (Hestrin, 1954) medium that consisted of 2 wt % D-glucose, 0.5 wt % peptone, 0.5 wt % yeast extract, 0.27 wt % disodium phosphate, 0.115 wt % citric acid (monohydrate), and distilled water was the growth medium of the cellulose-producing bacterium. The medium pH was adjusted to about 5.0 using hydrochloric acid. The first batch comprising 150 grams of water and the rest of the Hestrin-Schramm reagents was placed in a 250 ml flask and was autoclaved at 121° C. for 15 minutes, then cooled before it was inoculated with the bacterium strain. The inoculated medium was placed in the incubator at temperatures about 28° C. to 30° C. The first batch was cultured in static environment to produce a starter culture that would be used to inoculate the media for nanocomposites. The starter culture was grown for about 1 week. At such time, a thin cellulose film has materialized in the air-liquid interface.

Nanocomposites. Nanocomposites are the resultant materials from these experiments but the formed materials will be referred to herein as products. To produce the products, PEO was added to Hestrin-Scramm medium in 0.5, 1, 2, 3, and 5 wt %. The medium was autoclaved the same way as the starter culture. Incubation in static environment was done for 1 day of which a very thin pellicle appeared in the air-liquid interface. The pellicle was taken out and squeezed to capture the bacteria-rich suspensions. These bacteria-rich suspensions were used to start the growth of the products. The cellulose fibrils were bacterial-synthesized in magnetically stirred environment to promote interaction of the polymer and cellulose during growth and crystallization. Strings of materials started appearing on the second day of growth period. After 3 to 7 days, the medium appeared to be filled up with white cotton-like substance. The white cotton-like substances were the products. These products were then harvested by filtering the growth medium in cheesecloth. After washing the products with distilled water, it was molded in rectangular plastic cellophane and frozen for about 24 hours. The frozen material was then freeze-dried overnight or about 12 hours. Dried products were weighted to obtain its yield then flattened into thin sheets for characterizations. All products were kept in vacuumed desiccators prior to characterization to keep them dry.

Two different molecular weights of PEO were used to make nanocomposites. PEO of molecular weight 100,000 grams/mole and 600,000 grams/mole were chosen and are referred as PEO1 and PEO6 respectively. The polymer PEO was an Acros Organic reagent purchased from Fisher Scientific and was used without further purification. The weight percentages of PEO added to the growth medium are referred as the initial amount of PEO.

Characterization Methods:

TEM. TEM is done to look at the dispersion of cellulose fibrils in the wet state. The samples were taken out from the suspensions that developed with the products and were set in the 400-mesh copper TEM grid. The loaded grid was lightly washed with distilled water, dried and stained with 1% uranyl acetate. TEM inspection was done with JEOL 1200 EX operated at 100 kV. Images were taken at 60K magnification. Diameters of cellulose fibrils were measured by utilizing the arbitrary measurement function that came with the TEM software.

TGA. To determine the chemical compositions of the final freeze-dried product, TGA was utilized. TGA is a thermal weight change instrument that is used to measure the amount and rate of change in weight of a sample as a function of increasing temperature. Weight percent change and derivative data can be obtained from TGA of which then can be used to determine weight percentages and degradation temperatures of the components in the sample. The method of determination of weight percentages and degradation temperatures is complied from ASTM E 1131. The dried products were cut into very small pieces and about 10 to 25 milligrams was loaded into the aluminum TGA pan. The product-filled pan was weighed and was positioned into the TGA hangdown. The TGA unit employed was Rhiometrics STA 625. A sample was left isothermally at 30° C. for 5 minutes then heated at the rate of 20° C./min in the range of 30° C. to 600° C. The heating was done under nitrogen gas environment to circumvent oxidation.

FT-IR. FT-IR analysis was used to determine molecular interaction between PEO and cellulose. Chemical reaction or molecular rearrangement can be evaluated by identifying frequency peaks appearance or shifts. Thin wet samples of products were freeze-dried for 8 hours and were analyzed by Nicolet Nexus 670 FT-IR machine in transmission mode with a resolution of 4 in the range 4000-600 $cm^{-1}$. Forty scans were done for each sample.

AFM. To continue looking at cellulose fibrils dispersion, the dry products can be monitored to perceive the manner of rearrangement of those fibrils as the products dried out. Very small rectangular-shaped thin sheet of freeze-dried product was glued into an AFM sample disc. Using a microtome, the exposed top of the sample was trimmed to get a smooth surface for topography and phase imaging. Veeco Multimode III was the AFM machine used with the J scanner and MPP tapping tips. Images were taken in open-air environment. Scan rate was 1.5, scan size was 2 μm with aspect ratio as 1. Integral and proportional gains were 0.3 and 0.5 respectively.

DSC. Tgs, Tm and ΔHf Determination. The thermal properties were used to confirm that nanocomposites are indeed produced from the disclosed methods. The appearance of two Tgs or changes in Tgs and Tms will provide confirmation. Differential Scanning Calorimetry was done with Mettler Toledo DSC 822e. Freeze-dried products about 7 to 15 milligrams were loaded into the DSC aluminum pan with cover. Products and pure PEO samples were heated from 25° C. to 100° C. at the rate of 20° C./min to erase its previous thermal history then cooled off to −100° C. at the rate of 30° C./min. It was heated again from −100° C. to 100° C. at the rate of 20° C./min to acquire the samples' thermal properties. Pure cellulose samples were heated from 25-180° C. at the rate of 20° C./min, cooled off to −50° C. at 30° C./min then heated again from −50° C. to 200° C. at 20° C./min. All DSC tests were done with gas nitrogen purged at 80 ml/min and cooled by liquid nitrogen.

Equilibrium Melting Temperature Determination. Equilibrium melting temperatures eliminate the morphological effects associated with melting point determination, which is usually due to changes in crystal perfection or geometry and different thermal histories of the samples. The equilibrium melting temperatures were acquired by extrapolation of the experimental curve of experimental Tm versus Tc to the theoretical curve corresponding to Tm=Tc. This method was done on the assumption that the crystals are perfect and of finite size and that no recrystallization takes place during the melting run (Silva, 1998). The same DSC machine and the same amounts of dried products were used to determine melting points. Thermal histories were deleted by heating the samples from 25° C. to 100° C. at the rate of 20° C./min and kept the sample at 100° C. for 5 minutes. Rapid cooling was done at the rate of 45° C./min from 100° C. to the desired isothermal crystallization temperature. Isothermal crystallization was done at temperatures 28, 34, 40, 46, 52 and 58° C. for 25 minutes. After the isothermal crystallization was completed, the samples were cooled to 20° C. at 10° C./min and heated again to 100° C. at 10° C./min for the determination of melting points.

DMA. DMA was used to determine the bulk mechanical property of the nanocomposites. DMA involves the application of an oscillating strain from a vibrating head, to a rectangular test samples. Samples that were previously pressed with pressure of 4000 psi in the small hydraulic press were cut into strips of dimensions 34±1×7±1×0.6±0.2 mm. Rhiometrics RSA II was used to do testing in tension mode. Each samples were heated at the rate of 20° C./min from 20° C. to 100° C. except for pure PEO samples which were heated only up to 55° C. to erase any previous thermal histories. Strain sweep tests were done at 30° C. and 1 Hz. The strain sweep was done to determine the linear visco-elastic boundary which was defined to be the strain causing 5% or less reduction of the initial E' (Turi, 1997). The sample was then cooled to −70° C. at the rate of 20° C./min and was left at −70° C. for 1 min. Temperature ramping was done at the range of −70° C. to 100° C. with the rate of 5° C./min at 1 Hz. Taking the mean modulus from −70° C. to 40° C. and comparing it with the modulus at 90° C. determined the decrease in the order of magnitude of modulus.

Results and Discussion

TEM. Dispersion is a primary challenge with nanocomposite fabrication, and the present invention provides a means to make highly dispersed fibrils in the polymer matrix. To see how cellulose fibrils disseminate into the PEO matrix, Applicants first looked at the fibril dispersion in wet state; when the fibrils were still within the growth medium right before the products were harvested. FIGS. 10 A-D show the images of cellulose fibrils taken from TEM machine.

From the images in FIGS. 10 A-D, bacterial cellulose fibrils grown in medium without PEO additive (FIG. 10A) seemed to be aggregated. Evident aggregated fibrils can be measured directly when the image was magnified to 100 K and some individual fibrils can also be distinguished and measured. Aggregated fibrils diameters were 94±3 nm and the individual fibrils were 17±5 nm. The individual fibril diameter coincides with the reported bacterial cellulose fibril diameter by Gilbert (Gilbert, 1994). When initial PEO1 of 1 wt % was added to the growth medium, the aggregated fibrils were still evident but as PEO increased into 3 wt % and 5 wt %, the aggregation seemed to lessen yet the fibrils were still held together that was believed to be by PEO1. With initial PEO1 of 1 wt %, the aggregated fibril which is the ribbon had diameters 49±6 nm, smaller than the cellulose ribbons grown without PEO1. The contours of the individual fibrils were apparent when cellulose fibrils were grown without PEO1 and until PEO1 initial amount was 3 wt %. When the initial PEO1 added was 5 wt %, the outline of individual fibrils seemed to fade and it looked like it was covered with a thin coat. This thin coat was believed to be PEO1 and as its amount became substantial, its texture now affects the cellulose fibril image but it is still invisible in the TEM image. PEO1 did affect the aggregation of cellulose fibrils and thus, this simply means that, physically, the addition of such polymer can increase dispersion of cellulose.

AFM. As seen from the TEM characterization, PEO1 did instigate dispersion with cellulose fibrils in the wet state. When the products dried, AFM was used to look into the morphology of the products by probing into its surface topography and phase. FIGS. 11 A-E depict the AFM images of cellulose and nanocomposites. Without PEO1, the diameters of the fibrils that can directly be measured were about 100-200 nm. These diameters correspond to the aggregated fibrils diameter measured in TEM, the resolution of AFM can distinguish only the aggregated fibrils and not the individual fibrils. As the amount of initial PEO1 added to the medium increased, the aggregated fibrils came together and formed thick-diameter pieces. When the amount of initial PEO1 was 5 wt %, the topography image less compelling, so phase image was used, and it looked flat. From the images, as PEO1 disrupts the aggregation of cellulose fibrils (as shown in TEM images), it also filled the gaps between fibrils and wrapped the fibrils. The indistinguishable contours of cellulose fibrils and the flattened look of the dried product with 5 wt % initial PEO1 was concluded to be due to the significant amount of PEO1. As PEO1 increased, the products tend to form more flattened and smoother surfaces as the fibrils were wrapped up or covered up by the smooth texture of PEO1. This was based on the physical properties of the products. Without PEO, cellulose is very brittle, it can be crushed into fine fibrils by crushing with a finger and the texture was very coarse. With PEO, the cellulose fibrils appear to be held together by the polymer (PEO) matrix and the products were resilient, bendable and surfaces were smoother. When looking at the aspect ratio (e.g., length/diameter ratio) of dried cellulose fibrils, applicants take into consideration the works of Podsiadlo (Podiadlo, 2005) and coworkers and compare the AFM images from that work with what we have although the polymer matrix was not PEO with the referred work. There is a difference between the aspect ratio of fibrils from that work with the products produced from the instant work since the cellulose fibrils used by the referred paper were prepared by acid hydrolysis. It was apparent that the aspect ratio of the cellulose fibrils produced by the instant work is greatly higher than the cellulose fibrils produced by hydrolysis. AFM illustrated the interaction of cellulose fibrils and PEO1 and also the dispersion of cellulose fibrils in the dried products, and provides a visual idea of the aspect ratio of the reinforcing fibrils.

Figure 12:
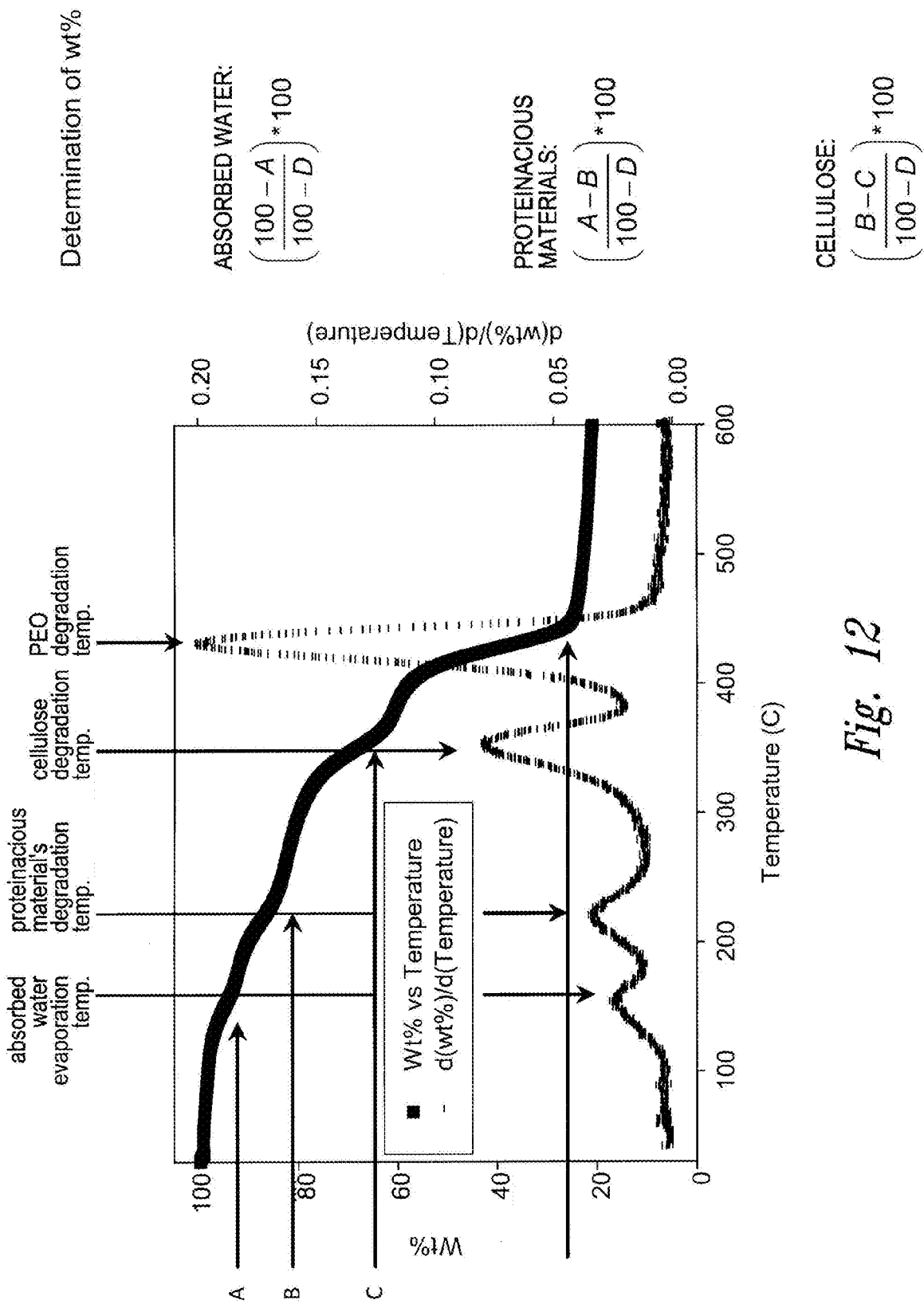
FIG. 12 shows, according to exemplary aspects, a sample analysis of TGA data, showing a method of determination of nanocomposite component wt %'s and degradation temperatures. The method complied with ASTM E 1131. The solid line in the graph represents variation of wt % as a function of temperature and the broken line is the derivative.
Figure 14:
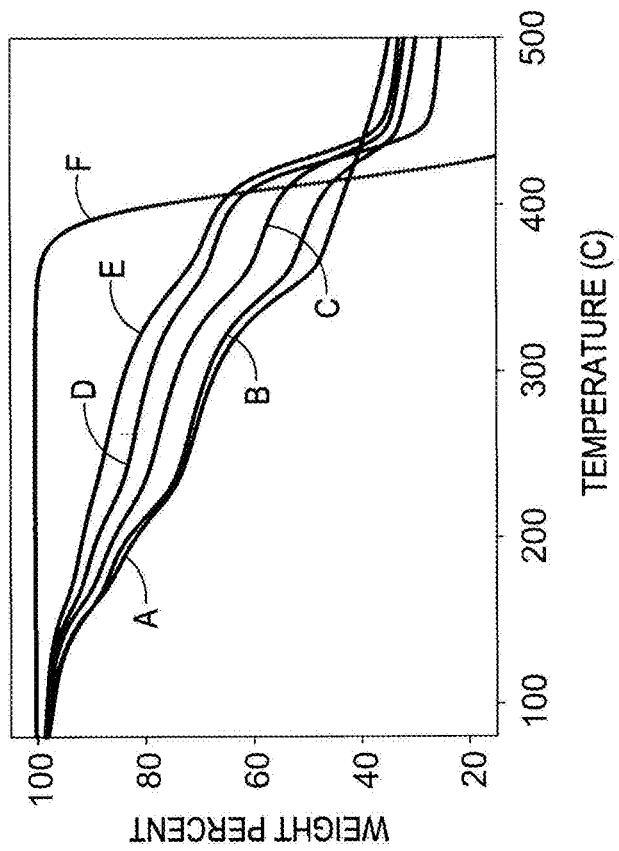
FIG. 14 shows, according to exemplary aspects, TGA data for cellulose/PEO6 nanocomposites. A) Pure cellulose; B) 0.5% wt initial PEO6; C) 1 wt % initial PEO6; D) 2 wt % initial PEO6; E) 3 wt % initial PEO6; and F) pure PEO6.
Figure 13:
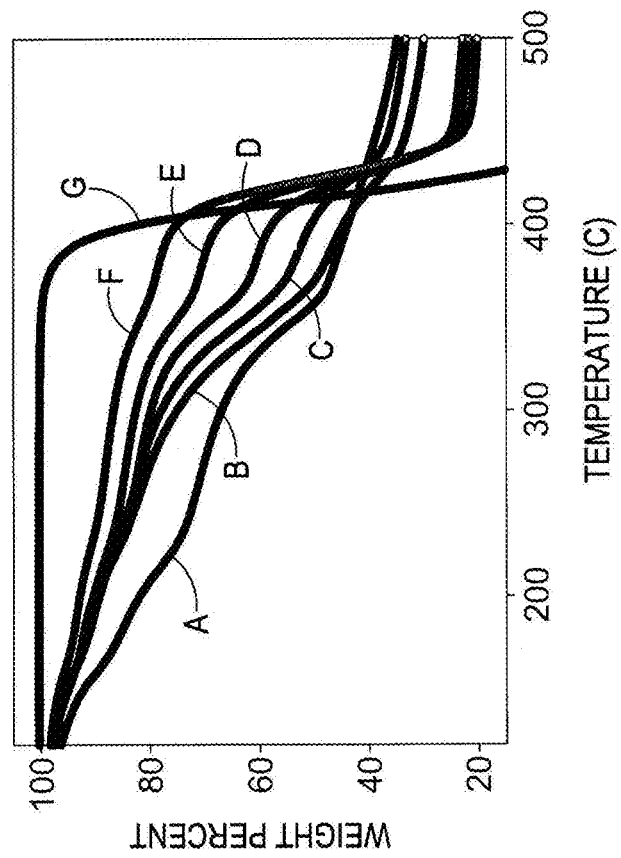
FIG. 13 shows, according to exemplary aspects, TGA data for cellulose/PEO1 nanocomposites. A) Pure cellulose; B) 0.5 wt % initial PEO1; C) 1 wt % initial PEO1; D) 2 wt % initial PEO1; E) 3 wt % initial PEO1; F) 5 wt % initial PEO1; and G) pure PEO1.

TGA. The enhancement of dispersion of cellulose fibrils when PEO was added has been demonstrated physically herein both in wet and dry states. The conception that PEO interacts with fibrils and therefore crystallizes therewith was confirmed by using TGA. TGA was used to determine the composition of the product by determining the degradation temperature of individual components in the product, namely PEO and cellulose. When two degradation temperatures appear, then both PEO and cellulose is in the product, thus a nanocomposite has formed. TGA will also provide the weight percent compositions of each components since the data obtained from the instrument is the change in weight of the product with respect to increasing temperature. Derivative data of weight percent over temperature changes were obtained to determine the degradation temperatures. A sample analysis of TGA data is shown in FIG. 12. The peaks of derivative data were used to determine the degradation temperatures of components. Weight percentages were determined by locating the temperatures of the plateau of the derivative data then associated such temperature to the weight percentage. FIGS. 13 and 14 illustrate the analyzed TGA data, and TABLE 2 enumerates the numerical data.

and nucleic acids also emerged from bacteria cells, thus the adsorbed water and proteinaceous materials derivative peaks appeared with pure cellulose. These amounts decreased as the amount of cellulose decreased in the nanocomposites. Proteinaceous materials degraded at about 220° C. The amount of these materials, which was 15%-20% was in accordance to the result obtained by George (George, 2005) and coworkers. The weight percentages were normalized with the ash content and the equations used were presented in FIG. 12. As TABLE 2 indicates, the amount of PEO in the nanocomposites increased as its initial amounts were increased.

Figure 15:
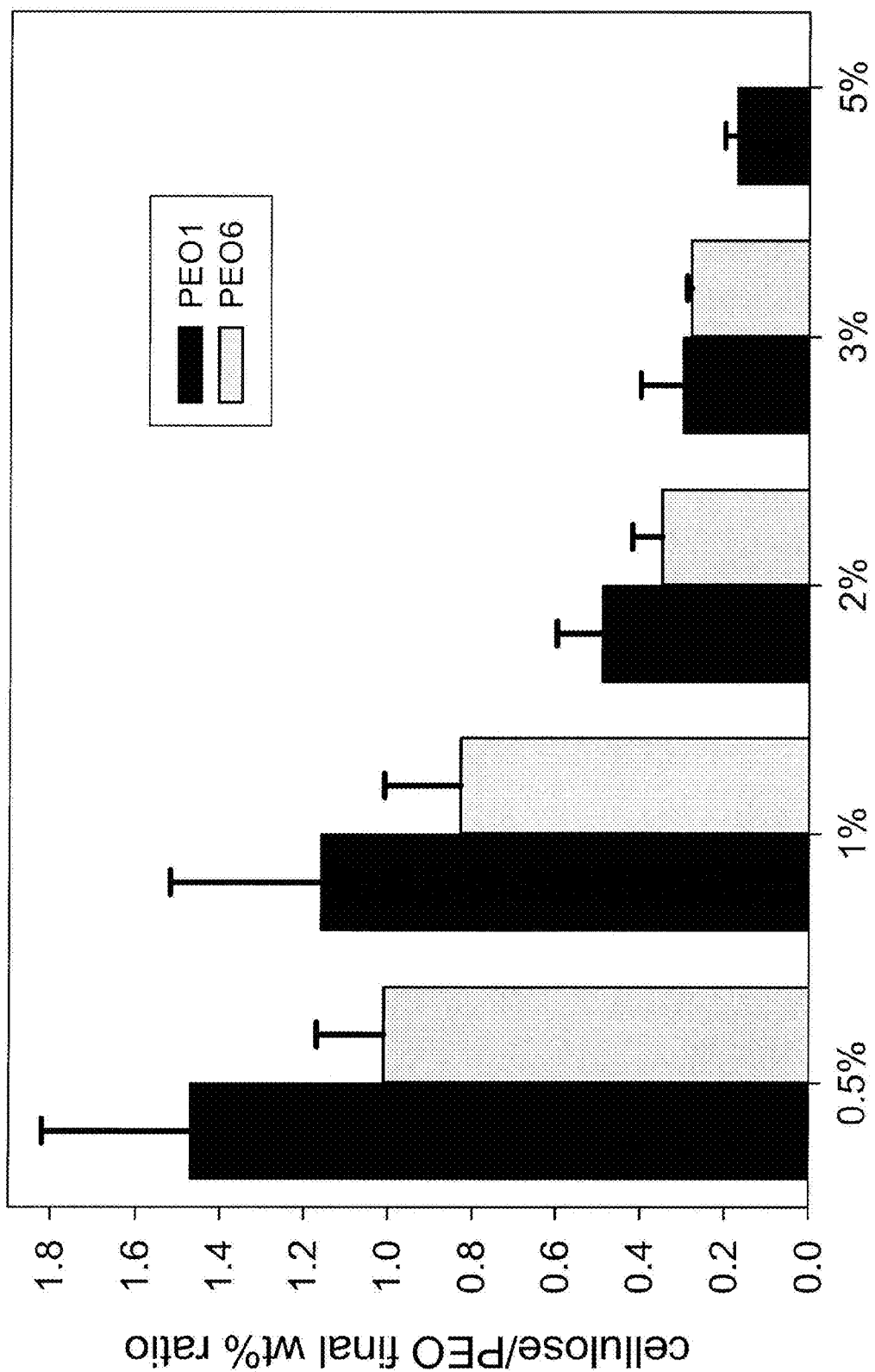
FIG. 15 shows, according to exemplary aspects, final cellulose/PEO wt % ratio with respect to the initial amount of PEO in the growth medium.

The amount of PEO and cellulose was of interest. FIG. 15 shows the ratio of cellulose over PEO in each sample, and the various compositions of nanocomposites can be identified with these ratios. The chemical compositions of the nanocomposites were altered as the growth environment of *Acetobacter xylinum* were varied. This occurrence simply confirms applicant's conception that nanocomposite compositions can be tuned by tuning the initial conditions of bacteria growth medium.

TABLE 2

TGA data for cellulose/PEO1 and cellulose/PEO6 nanocomposites

|  | Water wt % | Protein wt % | Cellulose wt % | PEO wt % |
|---|---|---|---|---|
| Cellulose | 18.9 ± 6.77 | 19.9 ± 6.34 | 87.7 ± 4.45 |  |
| Initial PEG wt % |  |  |  |  |
| W/0.5 PEO1 | 14.8 ± 6.37 | 15.7 ± 6.95 | 41.1 ± 6.36 | 28.4 ± 3.13 |
| W/1% PEO1 | 17.0 ± 2.45 | 13.3 ± 6.74 | 37.0 ± 8.23 | 32.7 ± 3.46 |
| W/2% PEO1 | 11.1 ± 1.35 | 13.2 ± 1.19 | 24.8 ± 4.33 | 50.9 ± 3.70 |
| W/3% PEO1 | 11.0 ± 1.96 | 11.1 ± 1.53 | 17.7 ± 4.14 | 60.2 ± 6.29 |
| W/5% PEO1 | 9.5 ± 1.68 | 7.8 ± 0.49 | 12.0 ± 1.75 | 70.7 ± 3.50 |
| Pure PEO1 | 0.0 | 0.0 | 0.0 | 100.0 |
| W/0.5% PEO6 | 18.2 ± 2.03 | 20.0 ± 2.50 | 31.0 ± 4.19 | 30.9 ± 1.18 |
| W/1% PEO6 | 17.1 ± 2.06 | 16.3 ± 0.28 | 30.0 ± 4.23 | 36.6 ± 2.74 |
| W/2% PEO6 | 13.0 ± 0.49 | 11.8 ± 0.45 | 19.4 ± 3.11 | 55.8 ± 2.74 |
| W/3% PEO6 | 13.7 ± 0.16 | 11.8 ± 0.39 | 16.5 ± 0.45 | 58.0 ± 1.00 |
| Pure PEO6 | 0.0 | 0.0 | 0.0 | 100.0 |

|  | Degradation of water (C) | Degradation of protein (C) | Degradation of cellulose (C) | Degradation of PEO (C) | Cellulose/PEO ratio |
|---|---|---|---|---|---|
| Cellulose | 158.5 ± 4.05 | 217.9 ± 3.51 | 346.4 ± 2.39 |  |  |
| Initial PEO wt % |  |  |  |  |  |
| W/0.5 PEO1 | 152.3 ± 3.96 | 219.4 ± 5.29 | 345.7 ± 6.96 | 425.9 ± 3.19 | 1.47 ± 0.35 |
| W/1% PEO1 | 157.8 ± 2.25 | 210.7 ± 25.76 | 350.7 ± 2.27 | 428.3 ± 3.48 | 1.16 ± 0.36 |
| W/2% PEO1 | 154.6 ± 3.99 | 218.0 ± 1.56 | 351.4 ± 1.76 | 428.6 ± 0.57 | 0.49 ± 0.11 |
| W/3% PEO1 | 159.2 ± 5.75 | 222.5 ± 3.55 | 351.6 ± 1.66 | 427.3 ± 1.46 | 0.30 ± 0.10 |
| W/5% PEO1 | 160.8 ± 0.99 | 224.9 ± 7.49 | 348.3 ± 4.30 | 425.3 ± 4.82 | 0.17 ± 0.03 |
| Pure PEO1 |  |  |  | 410.3 ± 0.74 | 0.0 |
| W/0.5% PEO6 | 155.9 ± 3.38 | 216.8 ± 3.01 | 346.1 ± 2.42 | 427.1 ± 3.92 | 1.01 ± 0.16 |
| W/1% PEO6 | 157.6 ± 3.45 | 206.0 ± 14.04 | 349.2 ± 2.41 | 429.7 ± 1.94 | 0.83 ± 0.18 |
| W/2% PEO6 | 160.2 ± 3.95 | 220.0 ± 4.20 | 346.8 ± 1.45 | 431.7 ± 0.65 | 0.35 ± 0.07 |
| W/3% PEO6 | 160.2 ± 3.13 | 220.4 ± 1.83 | 341.5 ± 13.07 | 423.9 ± 7.64 | 0.28 ± 0.01 |
| Pure PEO6 |  |  |  | 412.0 ± 0.47 | 0.0 |

Figure 16:
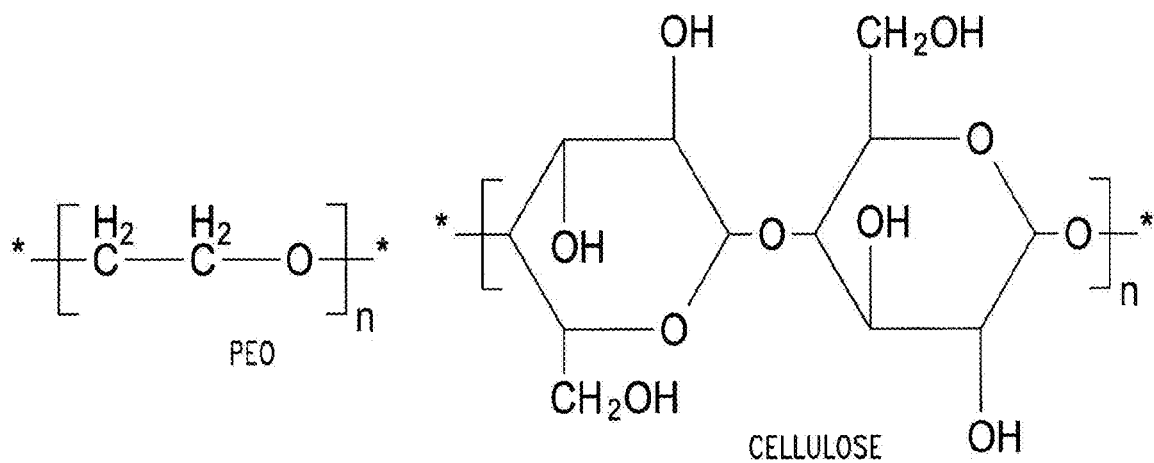
FIG. 16 shows, according to exemplary aspects, the molecular arrangement of PEO and cellulose.
Figure 17:
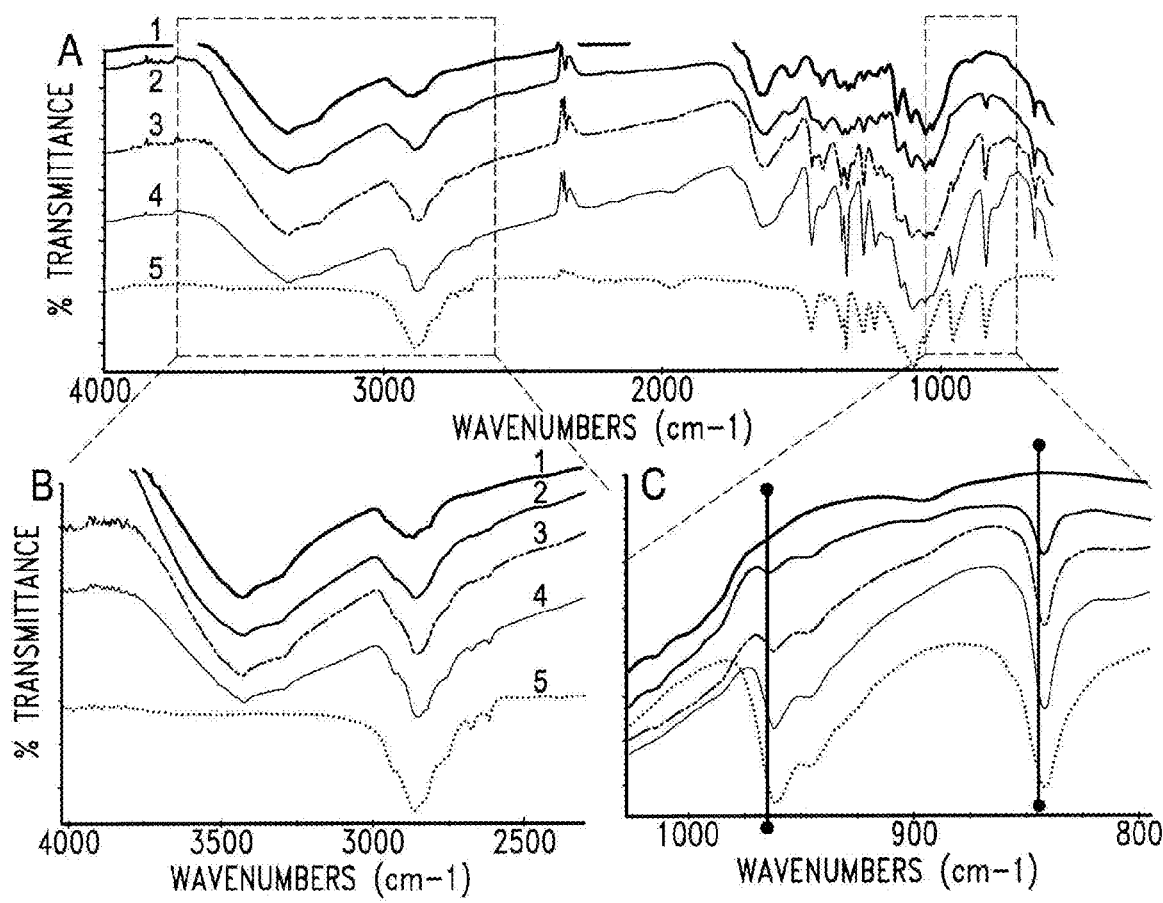
FIGS. 17 A-C show, according to exemplary aspects, FT-IR data of cellulose/PEO1 nanocomposites. In each spectrum, Cellulose/PEO1 final wt % ratio 1) pure cellulose, 2) 1.16, 3) 0.30, 4) 0.17, 5) 0 (Pure PEO1). A) Whole spectra and highlighted characteristic peaks; B) Peak at about 3300 that represents the O—H bond shows no shift or change in peak intensities when comparing cellulose and nanocomposites; and C) Peak at 963 $cm^{-1}$ and 842 $cm^{-1}$ represent C—H bend of PEO increased in intensity as the amount of PEO1 increased.

The derivative data displayed four peaks, which represented the evaporation of water, degradation of proteinacious materials, degradation of cellulose and degradation of PEO and the numerical data are presented in TABLE 2. Pure PEO and cellulose TGA data were obtained to determine the degradation temperature of pure materials. PEO1, PEO6 and cellulose degraded at 410.3±0.7° C., 412.0±0.5° C. and 346.4±2° C. respectively. The degradation temperatures that were present in both cellulose and PEO appeared in the TGA data of the products therefore it is now established that nanocomposites certainly were produced. Even though the nanocomposites were stored in vacuum-dried environment, adsorbed water comes with cellulose. Proteinacious materials FT-IR. Physical and chemical compositions of the products having been confirmed, the molecular interaction of cellulose and PEO was investigated. Information such as molecular rearrangement, types of bonding or reaction between the two components can reasonably be acquired by FT-IR. FIG. 16 depicted the molecules of cellulose and PEO, and FIGS. 17 A-C highlights the peaks of interests of FT-IR data. The whole spectra of the four samples, namely the pure cellulose and nanocomposites of cellulose/PEO1 final wt % ratio 1.16, 0.30 and 0.17 did not show very noticeable differences until some characteristic peaks were elaborated. Cellulose is recognized to form hydrogen bonding with other molecules so the peak at about 3300 was considered but there was no shift in the wave numbers and no intensity change thereby suggesting that no hydrogen bonding occurred between PEO1 and cellulose. There is however an indication of change in the intensity peaks at the wave numbers 963 cm$^{-1}$ and 842 cm$^{-1}$ (FIG. 17C) which represented the C—H out-of-phase bend of PEO1. Another peak that changed in intensity were the peaks at 1466 cm$^{-1}$, representing C—H2 bends. The peaks mentioned were constituents of the PEO molecule, thus it is expected that it would increase as the PEO amount in the nanocomposites increased. The ratio of peaks at 1360/1340 were seen to be decreasing as the amount of PEO increased. The 1360 peak is a cellulose constituent and 1340 was of PEO. Again, the variation of peak intensities was indicative of the relative amount of cellulose or PEO present in a sample, whether increasing or decreasing. There were no significant shifts of frequency peaks and there was no new peaks formed either which means that arrangement of molecules of cellulose and PEO were not altered and there was no chemical reaction between the two components. The interaction of cellulose and PEO that was seen in both TEM and AFM seemed to be instigated by Van der Waals forces, no hydrogen-bonding since there is no shifting in the O—H peaks.

Production. Now that the fabrication of nanocomposites was confirmed, it was beneficial to know some of the details of the production of this novel method of producing cellulose nanocomposites. Initial amounts of PEO added in wt % were; 0.5, 1, 2, 3 and 5. For PEO6, the maximum initial amount used was 3 wt %, and the medium was becoming very viscous. The nanocomposites are in the form of fibrous wet cotton-like material that can easily be molded into desired shape. Since the nanocomposites were freeze-dried, it produced a very porous material that can simply be compressed if compact material is intended. Pure cellulose is in the form of irregular granules and fibrils that when dried is brittle and can easily be crushed into powder. The nanocomposites are stretchy, and as the PEO amount is increased, plastic characteristic, elasticity that is, is more evident. As with the yield, when PEO is not added into the medium, about 32% of the D-glucose is converted to cellulose. When PEO is added, up to about 15% of D-glucose is transformed to cellulose and about 40% of the PEO were formed into the final nanocomposite. The yield seemed low but this is only for growing the nanocomposites for a maximum of 10 days. Also, nanocomposites can be grown again from the medium after the first harvest since some of the D-glucose and plastic is still present.

Figure 18:
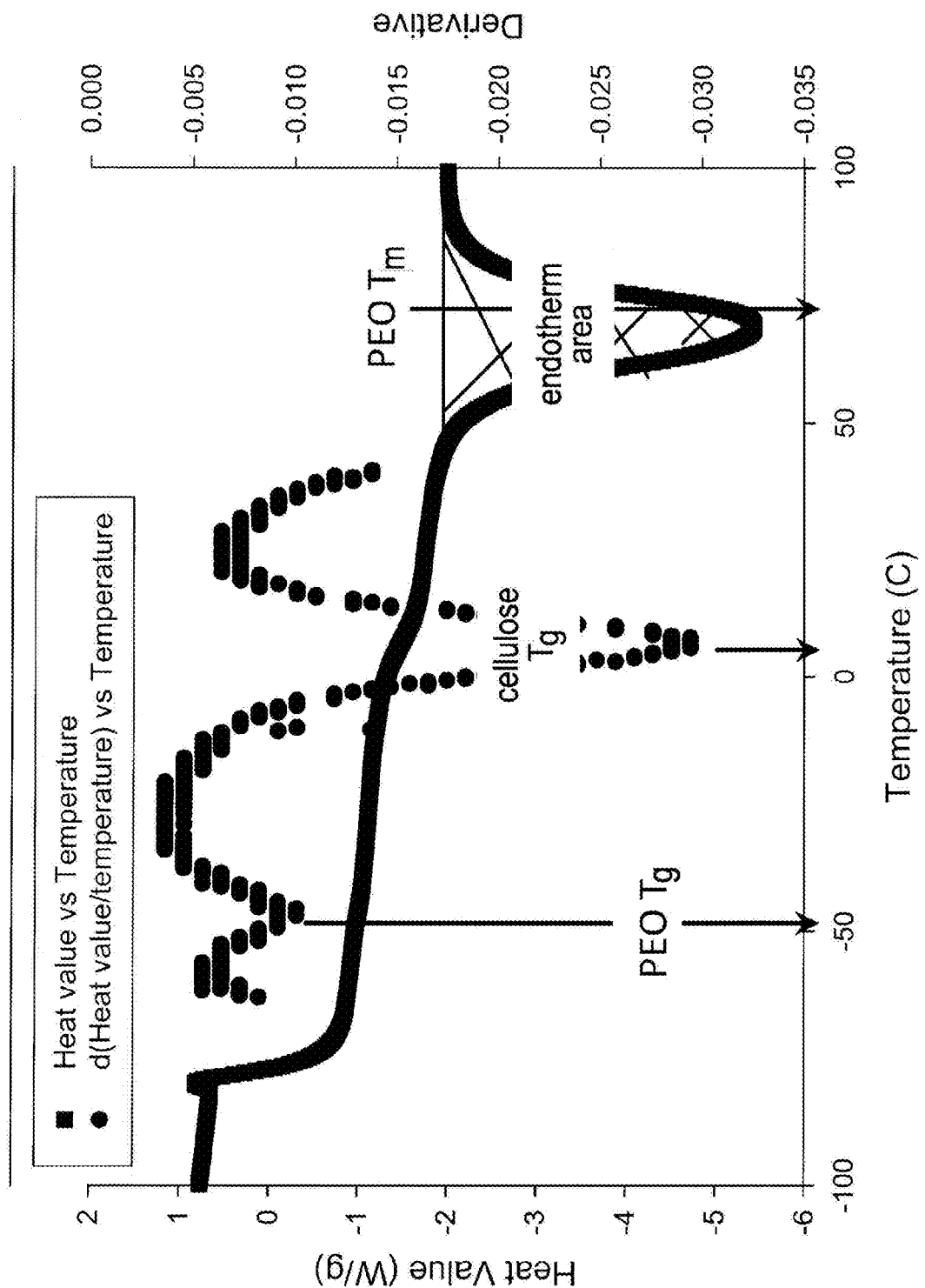
FIG. 18 shows, according to exemplary aspects, determination of cellulose/PEO nanocomposite thermal properties using the DSC data.
Figures 19A, 19B:
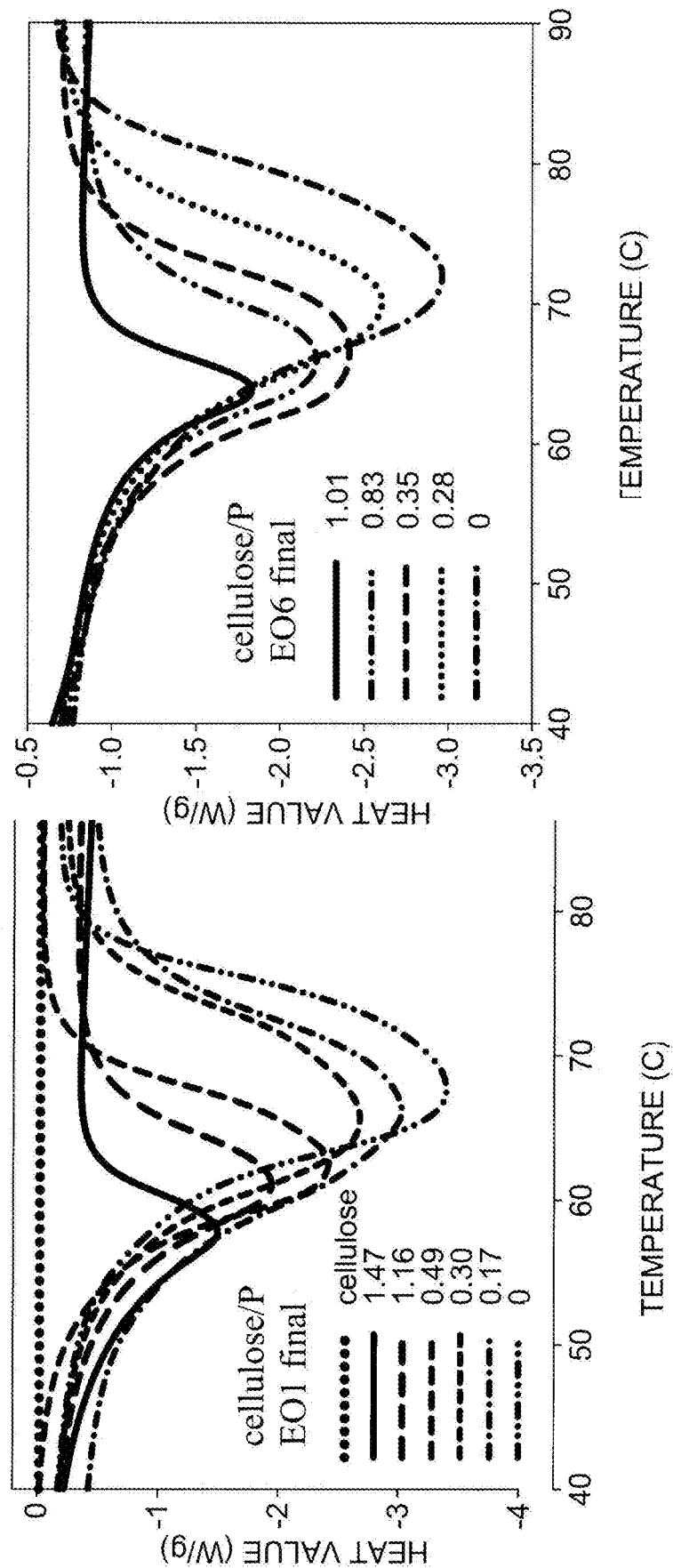
FIGS. 19 A-B show, according to exemplary aspects, DSC Data of: A) cellulose/PEO1; and B) cellulose/PEO6 nanocomposites. Heat value data were normalized by the PEO weight in the sample.
Figure 21:
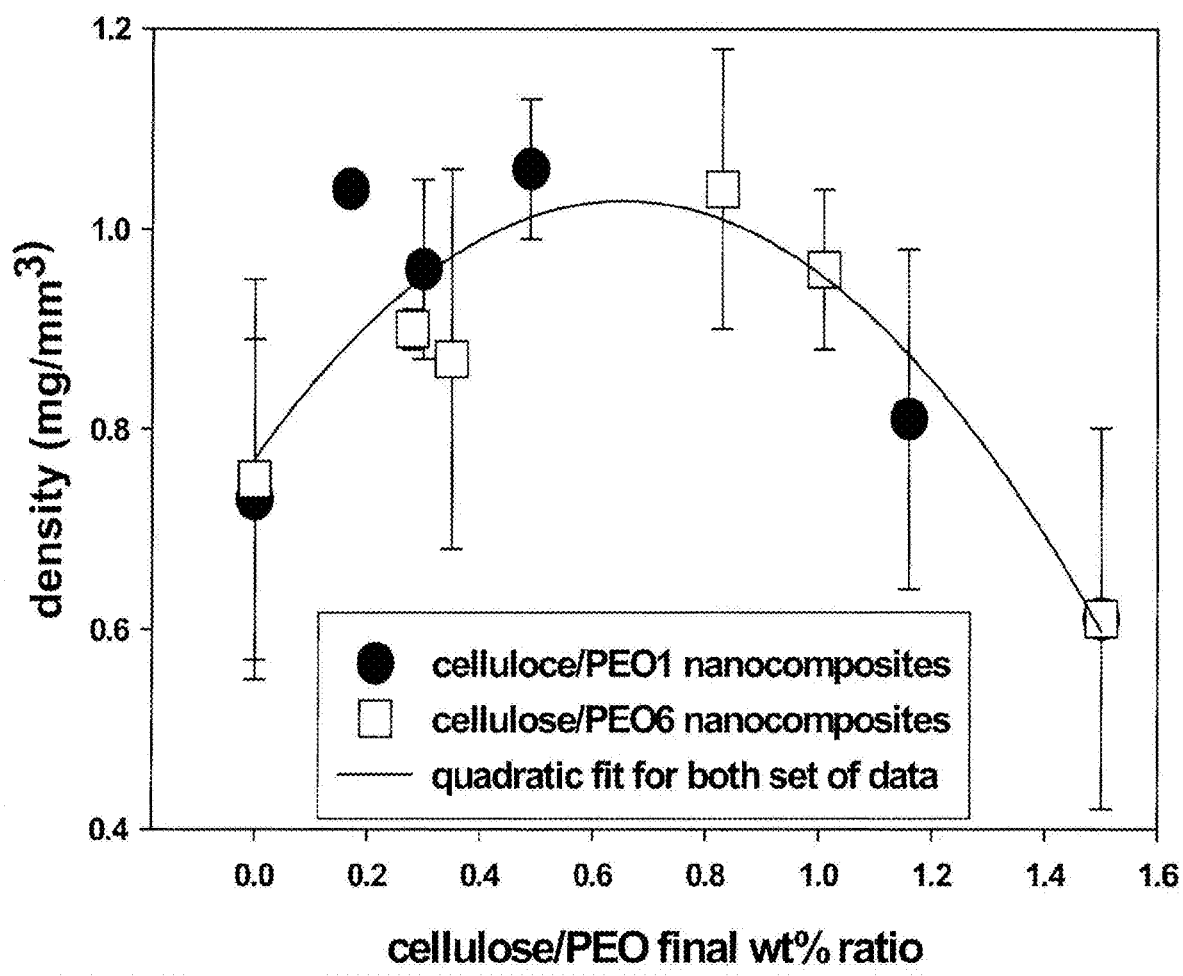
FIG. 21 shows, according to exemplary aspects, a density graph for: A) PEO1/cellulose nanocomposites; and B) PEO6/cellulose nanocomposites. The table on the left listed the numerical data from the graphs.

DSC. Determination of Tgs, Tms, and Crystallinity Index. Information such as Tg (glass transition temperature), Tm (melting temperature) and crystallinity index are some that can be determined from a DSC data. TABLE 3 lists this information taken from the sample DSC data and the representative DSC curves shown in FIGS. 19 A-B. In this experiment, Tg was estimated by taking two offset points from the inflection DSC segment and acquiring the midpoint between the offsets. Since the Tg values, especially of PEO were not very apparent, the derivative of heat value over temperature was used to perceive the inflection endpoints. Tm was projected as the lowest peak value of the endotherm curve. FIG. 18 illustrates the scheme for determining the thermal information. Crystallinity index was taken by integrating the endotherm curve to acquire its area and normalizing it with PEO sample weight then dividing the normalized integral by the ΔHf of pure PEO which was 201.22 J/g (James, 1999). Normalization of the integrated endotherm curve was done by dividing the integrated heat value by the weight of the sample multiplied by the final wt % of PEO (determined from TABLE 3) in such sample. The integrated endotherm peak area was determined from the software that came with the DSC machine.

TABLE 3

DSC Data for cellulose/PEO nanocomposites.

| | PEO Tg (C) | Tm (C) | Crystallinity Index |
|---|---|---|---|
| Cellulose (w/proteinacious mat'ls) cellulose/PEO final wt % ratio | 15.9 ± 2.3 | 168.0 ± 7.7 | |
| 1.47 | −50.1 ± 5.6 | 59.8 ± 1.4 | 0.21 ± 0.1 |
| 1.16 | −49.7 ± 3.7 | 61.7 ± 3.1 | 0.36 ± 0.2 |
| 0.49 | −48.4 ± 1.0 | 63.2 ± 1.3 | 0.49 ± 0.0 |
| 0.30 | −48.4 ± 3.0 | 66.1 ± 4.6 | — |
| 0.17 | −51.0 ± 2.0 | 68.1 ± 2.8 | 0.49 ± 0.1 |
| Pure PEO1 | −52.4 ± 0.4 | 68.1 ± 0.6 | 0.67 ± 0.0 |
| 1.01 | −49.7 ± 3.8 | 64.1 ± 2.0 | 0.21 ± 0.0 |
| 0.83 | −54.1 ± 2.0 | 65.4 ± 3.3 | 0.26 ± 0.1 |
| 0.35 | −53.5 ± 1.4 | 66.1 ± 1.3 | 0.40 ± 0.0 |
| 0.28 | −52.6 ± 2.5 | 69.7 ± 3.2 | 0.38 ± 0.1 |
| Pure PEO6 | −52.1 ± 0.8 | 71.1 ± 0.8 | 0.59 ± 0.0 |

Cellulose samples were processed in different DSC heating parameters. Without being preheated, the first cellulose Tg was determined by heating the bacterial cellulose from −150° C. to 250° C. at the rate of 20° C./min. Tg turned out to be about 16° C.±3 which corresponds to George (George, 2005) and coworkers' result of 13° C. and a melting point at about 168° C. that represents the proteinacious and nucleic acid materials. As the proteinacious materials were burned out by heating up the cellulose sample up to 180° C. and then obtaining the Tg by reheating the sample from −50° C. to 200° C. at the rate of 20° C./min, the Tg value became 60° C.±5° C. and no melting endotherm had materialized. The increase of Tg and the disappearance of Tm could possibly be a consequence to losing the adsorbed water and proteinacious materials of which then established a more bonded cellulose units. Nanocomposites were heated from 25-100° C. at the rate of 20° C./min to erase any previous thermal history of PEO since only PEO has evident melting point, cooled off to −100° C. at 30° C./min then heated again from −100° C. to 100° C. at the rate of 20° C./min to obtain the thermal information. Since the samples were heated differently from the cellulose, the Tg for cellulose was now around 20-30° C. We cannot necessarily extrapolate the effects of PEO to cellulose Tg since the DSC data gave a very diverse result. The big variation of cellulose Tgs might have been brought about by different thermal histories of cellulose and the proteinaceous materials since thermal history of these materials in the nanocomposite was not really erased as the sample was heated up to only 100° C. To erase the thermal history of cellulose, the sample was heated up to about 180° C. The nanocomposites exhibit PEO Tgs very close to pure PEO, this result actually agreed with the studies done by many researchers such as George and coworkers (George, 2005); that cellulose does not alter the Tg of PEO. PEO was the only component that has a melting endotherm and as the amount of PEO in the nanocomposites decreased, its Tm also decreased. The decrease of Tm could mean intimate interaction between the two components but this interaction can be quantified by knowing the equilibrium melting points and performing the Hoffman-Weeks (Hoffman, 1962) analysis. Without quantifying, the decrease in melting points could be presumed to be caused by the disorder or disarrangement of PEO crystalline units as the cellulose fibrils integrate into the PEO matrix. The decrease in crystallinity index substantiated the theory of crystal disarrangement. The supposition that crystalline arrangements of PEO were altered was also substantiated when the crystalline unit cell properties of each component were measured. Cellulose has the following cell dimensions: a=8 Å-9.35 Å; b=10.3 Å; c=8 Å-7.9 Å monomers/unit cell=2 [Mark 1999] while PEO has the following: a=7 Å-9.5 Å; b=13 Å-19.5 Å; c=12 Å-20 Å monomer/unit cell=28-36 (Mark 1999). PEO has a larger unit cell thus it is possible for cellulose to incorporate into the PEO crystal. With DSC data, cellulose and PEO interaction and distribution can thus be assessed.

Equilibrium Melting Temperature. To further verify that the melting point depression was not just a morphological effect, equilibrium melting points were obtained for pure PEO1 and nanocomposite of cellulose/PEO1 final wt % ratio 1.16 (FIG. 20). These two samples were chosen to verify that the equilibrium melting point of PEO indeed depress as bacterial cellulose fibrils incorporated into the crystals of PEO. Data of this analysis is presented in FIG. 20. Equilibrium temperatures were extrapolated using the linear fit of the experimental data of Tm versus Tc and the theoretical line corresponding to Tm=Tc. The equation of the linear fit ax+b=y where a is the slope, x is the crystallization temperature, b is the y-intercept and y is the melting temperature of the line was equated to the theoretical line y=x where again y is the melting temperature and x is the crystallization temperature. When the two equation were equated; ax+b=x, the value of x was determined, which would be the same as y of which this same value is the equilibrium melting temperature. Data of pure PEO1 and nanocomposite had the linear fit equations 0.208x+57.69 and 0.1644x+53.23 respectively. Equilibrium melting temperatures were 72.8° C. for pure PEO1 and 63.7° C. for the nanocomposite. There is indeed an obvious decrease in melting point verifying the modification of crystal arrangement or morphology of PEO1 crystals as cellulose fibrils associate with the polymer. DSC data thus established a nanoscale interaction between bacterial cellulose and PEO1 as crystal arrangement of PEO was altered.

Figure 22:
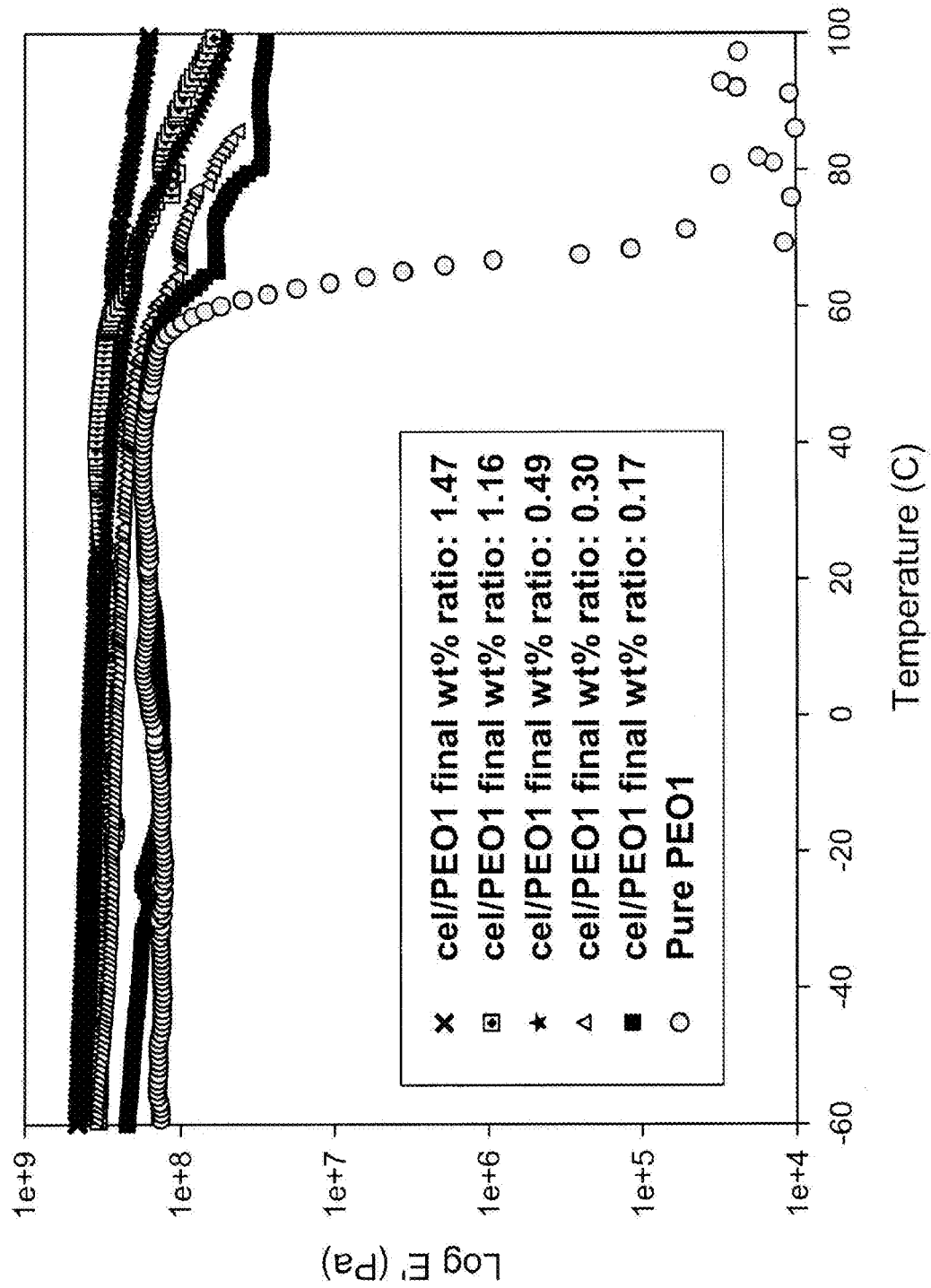
FIG. 22 shows, according to exemplary aspects, DMA Data of cellulose/PEO1 nanocomposites.
Figure 23:
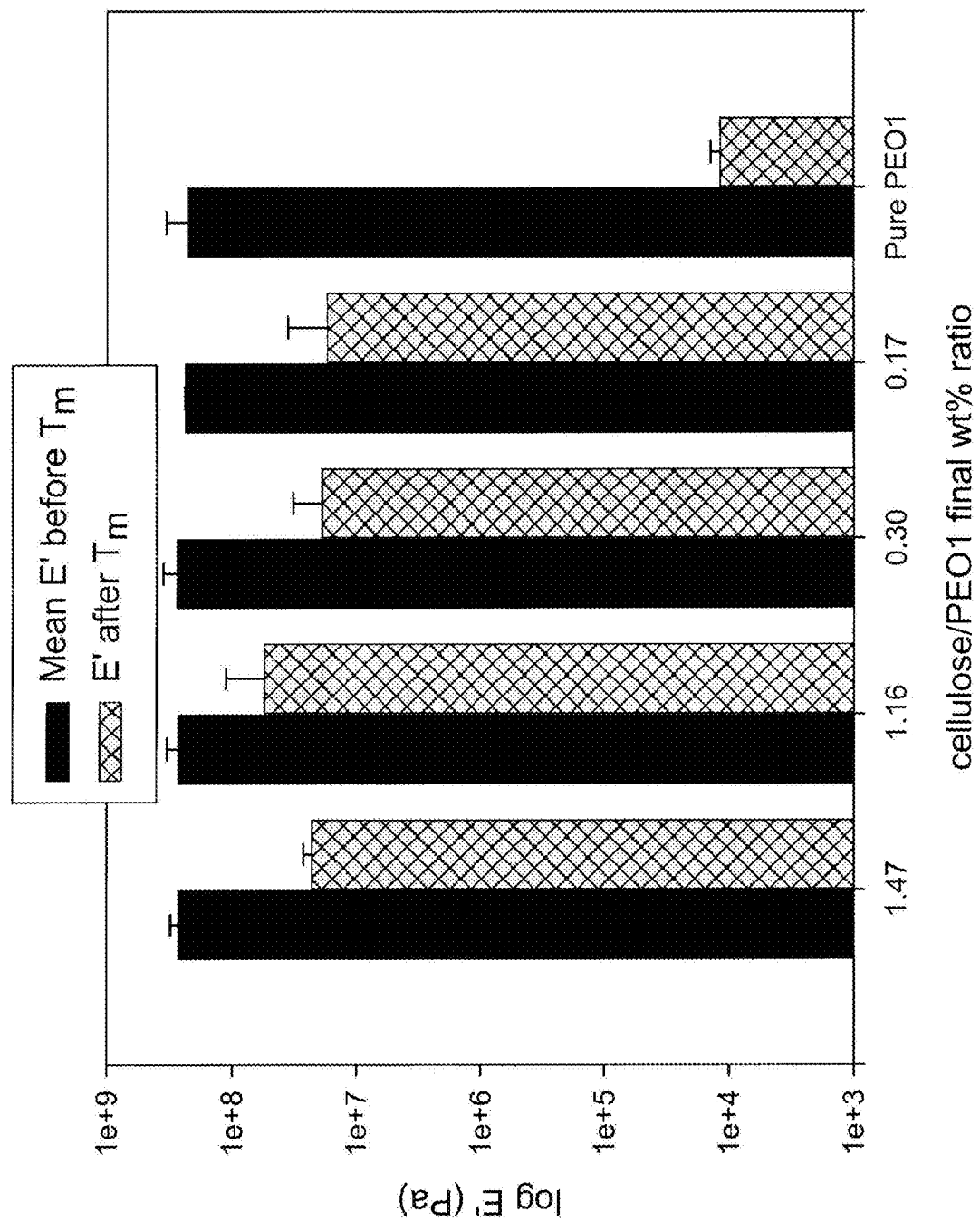
FIG. 23 shows, according to exemplary aspects, comparison of storage modulus (E') of cellulose/PEO1 before and after melting point temperature ($T_m$).

DMA. As seen in FIGS. 22 and 23, the storage modulus of both pure PEO1 and cellulose/PEO1 nanocomposites remained constant from −70° C. to about 60° C., which is approaching the melting temperature. At the melting temperature, the modulus drop of pure PEO1 was about 4 orders of magnitude. With the nanocomposites, the modulus drop is only about 1 order of magnitude. Cellulose provided PEO thermal stabilization (Samir, 2005a) of storage modulus at temperatures higher than Tm. The modulus of the nanocomposites were only slightly higher than the pure PEO1 and it also slightly increased as the amount of cellulose was increased. A confident conclusion that modulus increase transpired as cellulose amount increase cannot be implemented with the results acquired since the variations were very insignificant and standard deviation values of modulus were high. The high deviation of modulus might also be caused by the density deviation of samples presented in TABLE 4. The values of these densities are relative and not the absolute densities of the samples. There will be a big deviation in densities for the reason that although the researchers tried to uniformly fill the plastic cellophane with the wet products prior to freezing it, it is uncertain that the amounts of all samples were the same. The samples were pressed with uniform pressure, 4000 psi, in a hydraulic press after freeze-drying the harvested product so there is a possibility that the sides of the this sheets had smaller densities than those in the middle.

TABLE 4

Density variation of nanocomposite materials.

| Material final wt % ratio | Density |
| --- | --- |
| cellulose | 0.61 ± 0.19 |
| 1.16 | 0.81 ± 0.17 |
| 0.49 | 1.06 ± 0.07 |
| 0.3 | 0.96 ± 0.09 |
| 0.17 | 1.04 ± 0.01 |
| 0 | 0.73 ± 0.16 |
| cellulose/PEO6 final wt % ratio | |
| 1.01 | 0.96 ± 0.08 |
| 0.83 | 1.04 ± 0.14 |
| 0.35 | 0.87 ± 0.19 |
| 0.28 | 0.90 ± 0.02 |
| 0 | 0.75 ± 0.20 |

Example summary. Novel methods of producing cellulose nanocomposites have been achieved and disclosed herein. The methods enable production of nanocomposites with nanoscale cellulose fibrils that are very dispersed, thus unexpectedly solving a problem in the related art. The results were confirmed by TEM and AFM images. The cellulose fibrils were dispersed as PEO was added in the growth medium. The DSC data also established the interaction of cellulose and PEO with the depression of melting points and crystallinity. DMA data validated the interaction of cellulose and PEO because of the thermal stabilization of PEO which can be claimed from the good stress transfer caused by dispersed cellulose fibrils in the PEO matrix. Tailoring properties (e.g., fibril length, diameter, aspect ration, density, modulus, etc.) of the produced nanocomposites was accomplished by i) variation of chemical composition of final dried nanocomposites, ii) changes in thermal properties and crystallinity of PEO. The variation of nanocomposite properties was done by altering the composition of the bacterium growth medium. The alteration was done by addition of varying amounts of PEO into the medium. TGA data revealed the variation of compositions as the amounts of PEO added to the medium were varied. The chemical composition variation was supported by the FT-IR data that showed the shifting frequencies of some characteristics peaks of PEO and cellulose. DSC data explicitly exhibit the changes in thermal properties and crystallinity of PEO, which simply means that the PEO crystallites were altered by the cellulose fibrils. The modification of PEO crystals denotes a nanoscale strong interaction of cellulose and PEO molecules. The process of nanocomposite production used in this Example has been illustrated using water-soluble polymers that do not significantly hinder growth of cellulose-producing bacteria. Alternatively, less soluble or non-soluble polymers materials can be used with utilization of surfactants and/or other solubilizing agents.

CITED REFERENCES

Incorporated Herein in their Entirety

Jonas, Rainer; Farah, Luiz "Production and Application of Microbial Cellulose" *Polymer Degradation and Stability*, 59, 101-106 (1998).
Cannon, R. E.; Anderson, S. M. *Crit. Rev. Microbiol.*, 1991, 17, 435.
Haigler, Candace H.; Brown, R. Malcolm, Jr; Benziman, M. "Calcofluor White ST Alters in vivo Assembly of Cellulose Microfibrils" *Science*, 210, 903-906 (1980).

Uhlin, K. Ingegerd, Atalla, Rajai H., Thompson, Norman S. "Influence of hemicellulose on the aggregation patterns of bacterial cellulose" (1995) *Cellulose* 2, 2, 129-144.

Haigler, Candace H., White, Alan R., Brown, Malcolm R. (1982) "Alteration of In Vivo Cellulose Ribbon Assembly by Carboxymelthycellulose and Other Cellulose Derivatives" The *Journal of Cell Biology* 94, 64-69.

Colvin, J R, Witter D E. (1983) *Protoplasma* 116, 34-40.

Yamamoto, Hiroyuki, Horii, Fumitaka, Hirai, Asako. "In situ crystallization of bacterial cellulose II. Influences of different polymeric additives on the formation of celluloses I$\alpha$ and I$\beta$ at the early stage of incubation" (1996) *Cellulose* 3, 4, 229-242.

Yamamoto, H., Horii, F. (1994) *Cellulose* 1, 1, 57-66.

Ohad, I. (1963) *Bulletin of Research Council Of Israel* 11A, 4 279-285.

Whitney, Sarah E., Gothard, Michelle G., Mitchell, John T., Gidley, Michael J. (1999) *Plant Physiology* 121, 657-663.

Astley, Owen M., Chaliaud, Elisabeth, Donald, Athene M., Gidley, Michael J. (2003) *International Journal of Biological Macromolecules* 32, 28-35.

Whitney, Sarah E. C.; Brigham, Jennie E.; Darke, Arthur H.; Reid, J. S. Grant; Gidley, Michael J.; "Structural aspects of the interaction of mannan-based polysaccharides with bacterial cellulose" *Carbohydrate Research*, 307, 299-309 (1998).

Samir, My Ahmed Said Azizi; Alloin, Fannie; Dufresne, Alain "Review of Recent Research into Cellulosic Whiskers, Their Properties and Their Application in Nanocomposite Field" (2005) *Biomacromolecules.* 6, 2, 612-626.

Smart, S. K.; Cassady, A. I.; Lu, G. Q.; Martin, D. J. The biocompatibility of carbon nanotubes. *Carbon* (2006), 44(6), 1034-1047.

Favier, V. Chanzy, H., Cavaille, J. Y. "Polymer Nanocomposites Reinforced by Cellulose Whiskers" (1995) *Macromolecules* 28, 6365-6367.

Shoda, Makoto; Sugano, Yasushi "Recent Advances in Bacterial Cellulose Production" *Biotechnology and Bioprocess Engineering*, 10, 1-8 (2005).

Orts, William J., Shey, Justin, Imam, Syed H., Glenn, Gregory M., Guttman, Mara E., Revol, Jean-Francois "Application of Cellulose Microfibrils in Polymer Nanocomposites" (2005) *Journal of Polymers and the Environment* 13, 4 301-306.

Coleman, Jonathan N.; Khan, Umar; Gun'ko, Yurii K. Mechanical reinforcement of polymers using carbon nanotubes. *Advanced Materials* (Weinheim, Germany) (2006), 18(6), 689-706.

Brown, Malcolm R. Jr. "The biosynthesis of cellulose" *Journal of Macromolecular Science, Pure and Applied Chemistry, A*33, 10, 1345-1373 (1996).

Czaja, Wojciech; Young David J.; Kawechi, Marek; Brown, R. Malcolm Jr "The Future Prospects of Microbial Cellulose in Biomedical Applications" *Biomacromolecules*, 8, 1, 1-12 (2007).

Biofill Ind Comer. Prod. Med. Hosp., Patent WO 08602095, 16 pp. (1986)

Biofill Produtos Biotechnol., Patent WO 08908148, 21 pp. (1989)

Klemm, Dieter; Schumann, Dieter; Udhardt, Ulrike; Marsch, Silvia "Bacterial Synthesized Cellulose—Artificial Blood Vessels for Microsurgery" *Progress in Polymer Science*, 26, 1561-1603 (2001).

Choi, Yong-Jin; Ahn, Yeonghee; Kang, Moon-Sung; Jun, Hong-Ki; Kim, In Soo; Moon, Seung-Hyeon "Preparation and Characterization of Acrylic Acid-Treated Bacterial Cellulose Cation-Exchange Membrane" *Journal of Chemical Technology and Biotechnology,* 79, 79-84 (2004).

Wan, Wan-Kei; Millon, Leonardo. Poly(vinyl alcohol)-bacterial cellulose nanocomposite. U.S. patent application Ser. No. 10/639,683 (published as 20050037082). Hydrogel-bacterial cellulose nano-composite materials are created using a hydrogel and never dried bacterial cellulose fibers.

Hestrin, S.; Schramm, M. "Synthesis of Cellulose by *Acetobacter xylinum* 2. Preparation of Freeze-Dried Cells Capable of Polymerizing Glucose to Cellulose" *Biochemical Journal,* 58, 345-352 (1954).

Silva, Marcia A.; de Paoli, Marco A.; Felisberti, M. Isabel "Flory-Huggins interaction parameter of poly(ethylene oxide)/poly(epichlorohydrin) and poly(ethylene oxide)/poly(epichlorohydrin-co-ethylene oxide) blends" *Polymer,* 39, 12, 2551-2556 (1998).

Turi, Edith A., Thermal Characterization of Polymeric Materials, $2^{nd}$ Edition, Vol. I, Academic Press, Brooklyn, N.Y., 1997, p 980.

Gilbert, Richard D. "Cellulosic Polymers Blends and Composites". Carl Hansen Verlag, New York, 1994.

Podsiadlo, Paul; Choi, Seok-Youl; Shim, Bongsup; Lee, Jungwoo; Cuddihy, Meghan; Kotov, Nicholas A. "Molecularly Engineered Nanocomposites: Layer-by-Layer Assembly of Cellulose Nanocrystals" *Biomacromolecules,* 6, 2914-2918 (2005).

George, Johnsy; Ramana, Karna Venkata; Sabapathy, Shanmugham Nadana; Jagannath, Jambur Hiriyannaiah; Bawa, Amarinder Singh. "Characterization of chemically treated bacterial (*Acetobacter xylinum*) biopolymer: Some thermo-mechanical properties" *International Journal of Biological Macromolecules,* 37. 189-194 (2005).

Mark, James E. (ed) "Polymer Data Handbook" Oxford University Press. New York: 1999.

Hoffman, John D; Weeks, James J "Melting Process and Equilibrium Melting Temperature of Polychlorotrifluoroethylene" (1962), *Journal of Research of the National Bureau of Standards*—A. Physics and Chemistry, 66A, 1, 13-28.

Samir, My Ahmed Said Azizi; Alloin, Fannie; Sanchez, Jean-Yves; Dufresne, Alain "Nanocomposite Polymer Electrolytes based on Poly(oxyethylene) and Cellulose Whiskers" *Polimeros:Ciencia e Tecnologia,* 15, 2 109-113 (2005).

The invention claimed is:

1. An in situ biosynthetic method for making a dispersed cellulose nanocomposite, comprising:

providing a growth medium comprising an amount of at least one polymer matrix material, the medium suitable for growth of cellulose-producing microbial or plant cells; and incubating the growth medium with the cells under conditions suitable to provide for in situ biosynthesis and concurrent dispersion of the fibrils in the medium and polymer matrix material to provide a cellulose nanocomposite material or film having a polymer content and in which the cellulose fibrils are highly and uniformly dispersed, and wherein at least one of cellulose fibril structure and composition of the nanocomposite material is determined, at least in part, by the amount or nature of the at least one polymer matrix material.

2. The method of claim 1, wherein determination of fibril structure comprises determination of at least one of fibril length, fibril diameter and fibril aspect ratio.

3. The method of claim 1, further comprising removing or separating the cellulose nanocomposite material or film from the medium.

4. The method of claim 3, further comprising washing the cellulose nanocomposite material or film to remove residual medium.

5. The method of claim 4, further comprising freeze-drying the cellulose nanocomposite material or film.

6. The method of claim 4, further comprising forming a molded product using the cellulose nanocomposite material or film.

7. The method of claim 1, wherein the polymer matrix material is present in an amount between about 1 wt % and about 10 wt % of the growth medium, and the polymer component of the cellulose nanocomposite material comprises from about 10 wt % to about 80 wt % of the produced cellulose nanocomposite material.

8. The method of claim 1, wherein the cellulose nanofiber diameter is between about 30 nm to about 130 nm, and wherein the cellulose nanofibers are highly dispersed and uniformly dispersed within the composite.

9. The method of claim 1, wherein the in situ synthesized cellulose comprises at least one of bacterial cellulose and plant cellulose.

10. The method of claim 9, wherein the cellulose comprises bacterial cellulose.

11. The method of claim 10 wherein the bacterial cellulose is that produced by *Acetobacter xylinum*.

12. The method of claim 1, wherein the polymer matrix material comprises at least one of a biobased polymer, a plant-derived polymer, a synthetic polymer and a thermoplastic polymer.

13. The method of claim 12, wherein the polymer matrix material comprises at least one selected from the group consisting of carboxymethyl cellulose (CMC), polyethylene oxide (PEO), polyvinyl alcohol (PVA), polybutadiene, polylactic acid (PLA), polyhydroxy alkanoates (PHAs), polyvinyl acetate, polyamides, nylons, polyacrylic acid (PAA), polypropylene, poly(ethylene-co-vinyl acetate) (EVA), poly(diallyldimethylammonium chloride) (PDDA), starch, acrylic resins, styrene-butyl acetate, Xylan, chitosan, poly(B-sydroxyoctanoate) (PHO), hemicellulose, phosphomannan, glucomannan, galactomannan, xyloglucan, and pectin.

14. The method of claim 13, wherein the polymer matrix material comprises at least one of polyethylene oxide (PEO) and polyvinyl alcohol (PVA).

15. The method of claim 13, wherein the polymer matrix material comprises polyethylene oxide (PEO).

16. The method of claim 1, wherein the growth medium comprises at least one of D-glucose, peptone, yeast extract, sodium diphosphate, citric acid, and citrate.

* * * * *